(12) United States Patent
Henley et al.

(10) Patent No.: US 9,186,443 B2
(45) Date of Patent: *Nov. 17, 2015

(54) WOUND TREATMENT APPARATUS

(71) Applicant: KCI MEDICAL RESOURCES, Grand Cayman (KY)

(72) Inventors: Alan Wayne Henley, Summerville, SC (US); Leigh Marie Moses, Summerville, SC (US); Ronald Leslie Sanderson, Charleston, SC (US); John Howard, Charleston, SC (US); James H. Price, Mount Pleasant, SC (US); Russell W. Bessette, Buffalo, NY (US)

(73) Assignee: KCI Medical Resources, Grand Cayman (KY)

( * ) Notice: Subject to any disclaimer, the term of this patent is extended or adjusted under 35 U.S.C. 154(b) by 0 days.

This patent is subject to a terminal disclaimer.

(21) Appl. No.: 14/030,735

(22) Filed: Sep. 18, 2013

(65) Prior Publication Data

US 2014/0025025 A1     Jan. 23, 2014

Related U.S. Application Data

(60) Continuation of application No. 12/860,581, filed on Aug. 20, 2010, now Pat. No. 8,540,687, which is a division of application No. 11/761,066, filed on Jun. 11, 2007, now Pat. No. 7,794,438, which is a division (Continued)

(51) Int. Cl.
    *A61M 1/00*           (2006.01)
    *A61M 35/00*        (2006.01)
(Continued)

(52) U.S. Cl.
CPC ........... *A61M 1/0031* (2013.01); *A61M 1/0025* (2014.02); *A61M 1/0027* (2014.02); *A61M 1/0088* (2013.01); *A61M 35/00* (2013.01); *A61F 2013/0017* (2013.01); *A61M 1/0058* (2013.01);

(Continued)

(58) Field of Classification Search
USPC ......... 604/289, 290, 317–319, 304–308, 291; 602/41–43, 2
See application file for complete search history.

(56) References Cited

U.S. PATENT DOCUMENTS

| 1,355,846 A | 10/1920 | Rannells |
| 2,547,758 A | 4/1951 | Keeling |

(Continued)

FOREIGN PATENT DOCUMENTS

| AU | 550575 A1 | 3/1986 |
| AU | 745271 | 4/1999 |

(Continued)

OTHER PUBLICATIONS

N.A. Bagautdinov, "Variant of External Vacuum Aspiration in the Treatment of Purulent Diseases of the Soft Tissues," Current Problems in Modern Clinical Surgery: Interdepartmental Collection, edited by V. Ye Volkov et al. (Chuvashia State University, Cheboksary, U.S.S.R. 1986);pp. 94-96 (certified translation).

(Continued)

*Primary Examiner* — Kim M Lewis

(57) ABSTRACT

A bandage has a first sheet overlying a wound and located adjacent to it and a top sheet overlying the first sheet. The first sheet has a plurality of discrete passageways overlying the wound and adapted to communicate negative pressure established by a negative pressure source to the wound.

30 Claims, 21 Drawing Sheets

Related U.S. Application Data of application No. 09/743,737, filed as application No. PCT/US99/17877 on Aug. 6, 1999, now Pat. No. 7,276,051, said application No. 11/761,066 is a division of application No. 09/369,113, filed on Aug. 5, 1999, now Pat. No. 6,458,109.

(60) Provisional application No. 60/095,625, filed on Aug. 7, 1998.

(51) Int. Cl.
 *A61F 13/00* (2006.01)
 *A61M 3/02* (2006.01)

(52) U.S. Cl.
 CPC .......... *A61M 3/0229* (2013.01); *A61M 2205/15* (2013.01); *A61M 2205/3344* (2013.01); *A61M 2205/366* (2013.01); *A61M 2205/368* (2013.01); *A61M 2205/3653* (2013.01)

(56) References Cited

U.S. PATENT DOCUMENTS

| | | | |
|---|---|---|---|
| 2,632,443 A | 3/1953 | Lesher | |
| 2,682,873 A | 7/1954 | Evans et al. | |
| 2,910,763 A | 11/1959 | Lauterbach | |
| 2,969,057 A | 1/1961 | Simmons | |
| 3,066,672 A | 12/1962 | Crosby, Jr. et al. | |
| 3,367,332 A | 2/1968 | Groves | |
| 3,520,300 A | 7/1970 | Flower, Jr. | |
| 3,568,675 A | 3/1971 | Harvey | |
| 3,648,692 A | 3/1972 | Wheeler | |
| 3,682,180 A | 8/1972 | McFarlane | |
| 3,826,254 A | 7/1974 | Mellor | |
| 4,080,970 A | 3/1978 | Miller | |
| 4,096,853 A | 6/1978 | Weigand | |
| 4,139,004 A | 2/1979 | Gonzalez, Jr. | |
| 4,165,748 A | 8/1979 | Johnson | |
| 4,184,510 A | 1/1980 | Murry et al. | |
| 4,233,969 A | 11/1980 | Lock et al. | |
| 4,245,630 A | 1/1981 | Lloyd et al. | |
| 4,250,882 A * | 2/1981 | Adair | 604/355 |
| 4,256,109 A | 3/1981 | Nichols | |
| 4,261,363 A | 4/1981 | Russo | |
| 4,275,721 A | 6/1981 | Olson | |
| 4,284,079 A | 8/1981 | Adair | |
| 4,297,995 A | 11/1981 | Golub | |
| 4,333,468 A | 6/1982 | Geist | |
| 4,373,519 A | 2/1983 | Errede et al. | |
| 4,382,441 A | 5/1983 | Svedman | |
| 4,392,853 A | 7/1983 | Muto | |
| 4,392,858 A | 7/1983 | George et al. | |
| 4,419,097 A | 12/1983 | Rowland | |
| 4,465,485 A | 8/1984 | Kashmer et al. | |
| 4,475,909 A | 10/1984 | Eisenberg | |
| 4,480,638 A | 11/1984 | Schmid | |
| 4,525,166 A | 6/1985 | Leclerc | |
| 4,525,374 A | 6/1985 | Vaillancourt | |
| 4,540,412 A | 9/1985 | Van Overloop | |
| 4,543,100 A | 9/1985 | Brodsky | |
| 4,548,202 A | 10/1985 | Duncan | |
| 4,551,139 A | 11/1985 | Plaas et al. | |
| 4,569,348 A | 2/1986 | Hasslinger | |
| 4,605,399 A | 8/1986 | Weston et al. | |
| 4,608,041 A | 8/1986 | Nielsen | |
| 4,640,688 A | 2/1987 | Hauser | |
| 4,655,754 A | 4/1987 | Richmond et al. | |
| 4,664,662 A | 5/1987 | Webster | |
| 4,710,165 A | 12/1987 | McNeil et al. | |
| 4,733,659 A | 3/1988 | Edenbaum et al. | |
| 4,743,232 A | 5/1988 | Kruger | |
| 4,758,220 A | 7/1988 | Sundblom et al. | |
| 4,787,888 A | 11/1988 | Fox | |
| 4,795,428 A * | 1/1989 | Hwang | 604/73 |
| 4,826,494 A | 5/1989 | Richmond et al. | |
| 4,838,883 A | 6/1989 | Matsuura | |
| 4,840,187 A | 6/1989 | Brazier | |
| 4,863,449 A | 9/1989 | Therriault et al. | |
| 4,872,450 A | 10/1989 | Austad | |
| 4,878,901 A | 11/1989 | Sachse | |
| 4,897,081 A | 1/1990 | Poirier et al. | |
| 4,906,233 A | 3/1990 | Moriuchi et al. | |
| 4,906,240 A | 3/1990 | Reed et al. | |
| 4,919,654 A | 4/1990 | Kalt | |
| 4,941,882 A | 7/1990 | Ward et al. | |
| 4,953,565 A | 9/1990 | Tachibana et al. | |
| 4,969,880 A | 11/1990 | Zamierowski | |
| 4,985,019 A | 1/1991 | Michelson | |
| 5,037,397 A | 8/1991 | Kalt et al. | |
| 5,086,170 A | 2/1992 | Luheshi et al. | |
| 5,092,858 A | 3/1992 | Benson et al. | |
| 5,100,396 A | 3/1992 | Zamierowski | |
| 5,134,994 A | 8/1992 | Say | |
| 5,149,331 A | 9/1992 | Ferdman et al. | |
| 5,167,613 A | 12/1992 | Karami et al. | |
| 5,176,663 A | 1/1993 | Svedman et al. | |
| 5,215,522 A | 6/1993 | Page et al. | |
| 5,232,453 A | 8/1993 | Plass et al. | |
| 5,261,893 A | 11/1993 | Zamierowski | |
| 5,278,100 A | 1/1994 | Doan et al. | |
| 5,279,550 A | 1/1994 | Habib et al. | |
| 5,298,015 A | 3/1994 | Komatsuzaki et al. | |
| 5,342,376 A | 8/1994 | Ruff | |
| 5,344,415 A | 9/1994 | DeBusk et al. | |
| 5,358,494 A | 10/1994 | Svedman | |
| 5,437,622 A | 8/1995 | Carion | |
| 5,437,651 A | 8/1995 | Todd et al. | |
| 5,527,293 A | 6/1996 | Zamierowski | |
| 5,549,584 A | 8/1996 | Gross | |
| 5,556,375 A | 9/1996 | Ewall | |
| 5,607,388 A | 3/1997 | Ewall | |
| 5,636,643 A | 6/1997 | Argenta et al. | |
| 5,645,081 A | 7/1997 | Argenta et al. | |
| 6,071,267 A | 6/2000 | Zamierowski | |
| 6,135,116 A | 10/2000 | Vogel et al. | |
| 6,241,747 B1 | 6/2001 | Ruff | |
| 6,287,316 B1 | 9/2001 | Agarwal et al. | |
| 6,345,623 B1 | 2/2002 | Heaton et al. | |
| 6,488,643 B1 | 12/2002 | Tumey et al. | |
| 6,493,568 B1 | 12/2002 | Bell et al. | |
| 6,553,998 B2 | 4/2003 | Heaton et al. | |
| 6,814,079 B2 | 11/2004 | Heaton et al. | |
| 8,540,687 B2 * | 9/2013 | Henley et al. | 604/289 |
| 2002/0077661 A1 | 6/2002 | Saadat | |
| 2002/0115951 A1 | 8/2002 | Norstrem et al. | |
| 2002/0120185 A1 | 8/2002 | Johnson | |
| 2002/0143286 A1 | 10/2002 | Tumey | |

FOREIGN PATENT DOCUMENTS

| | | |
|---|---|---|
| AU | 755496 | 2/2002 |
| CA | 2005436 | 6/1990 |
| DE | 26 40 413 A1 | 3/1978 |
| DE | 43 06 478 A1 | 9/1994 |
| DE | 295 04 378 U1 | 10/1995 |
| EP | 0100148 A1 | 2/1984 |
| EP | 0117632 A2 | 9/1984 |
| EP | 0161865 A2 | 11/1985 |
| EP | 0358302 A2 | 3/1990 |
| EP | 1018967 B1 | 8/2004 |
| GB | 692578 | 6/1953 |
| GB | 2 195 255 A | 4/1988 |
| GB | 2 197 789 A | 6/1988 |
| GB | 2 220 357 A | 1/1990 |
| GB | 2 235 877 A | 3/1991 |
| GB | 2 329 127 B | 3/1999 |
| GB | 2 333 965 A | 8/1999 |
| JP | 4129536 | 4/1992 |
| SG | 71559 | 4/2002 |
| WO | 80/02182 | 10/1980 |
| WO | 87/04626 | 8/1987 |
| WO | 90/10424 | 9/1990 |
| WO | 93/09727 | 5/1993 |
| WO | 94/20041 | 9/1994 |

(56) References Cited

FOREIGN PATENT DOCUMENTS

| WO | 96/05873 | 2/1996 |
|---|---|---|
| WO | 97/18007 | 5/1997 |
| WO | 99/13793 | 3/1999 |

OTHER PUBLICATIONS

Louis C. Argenta, MD and Michael J. Morykwas, PhD; "Vacuum-Assisted Closure: A New Method for Wound Control and Treatment: Animal Studies & Basic Foundation"; Annals of Plastic Surgery, vol. 38, No. 6, Jun. 1997; pp. 553-562.
Susan Mendez-Eastmen, RN; "When Wounds Won't Heal" RN Jan. 1998, vol. 61 (1); Medical Economics Company, Inc., Montvale, NJ, USA; pp. 20-24.
James H. Blackburn, II, MD, et al; "Negative-Pressure Dressings as a Bolster for Skin Grafts"; Annals of Plastic Surgery, vol. 40, No. 5, May 1998, pp. 453-457.
John Masters; "Reliable, Inexpensive and Simple Suction Dressings"; Letters to the Editor, British Journal of Plastic Surgery, 1998, vol. 51 (3), p. 267; Elsevier Science/The British Association of Plastic Surgeons, UK.
S.E. Greer, et al "The Use of Subatmospheric Pressure Dressing Therapy to Close Lymphocutaneous Fistulas of the Groin" British Journal of Plastic Surgery (2000), vol. 53, pp. 484-487.
George V. Letsou, MD., et al; "Stimulation of Adenylate Cyclase Activity in Cultured Endothelial Cells Subjected to Cyclic Stretch"; Journal of Cardiovascular Surgery, vol. 31, 1990, pp. 634-639.
Orringer, Jay, et al; "Management of Wounds in Patients with Complex Enterocutaneous Fistulas"; Surgery, Gynecology & Obstetrics, Jul. 1987, vol. 165, pp. 79-80.
International Search Report for PCT International Application PCT/GB95/01983; Nov. 23, 1995.
PCT International Search Report for PCT International Application PCT/GB98/02713; Jan. 8, 1999.
PCT Written Opinion; PCT International Application PCT/GB98/02713; Jun. 8, 1999.
PCT International Examination and Search Report, PCT International Application PCT/GB96/02802; Jan. 15, 1998 & Apr. 29, 1997.
PCT Written Opinion, PCT International Application PCT/GB96/02802; Sep. 3, 1997.
Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.
Kostyuchenok, B.M., et al; "Vacuum Treatment in the Surgical Management of Purulent Wounds"; Vestnik Khirurgi, Sep. 1986, pp. 18-21 and 6 page English translation thereof.
Davydov, Yu. A., et al; "Vacuum Therapy in the Treatment of Purulent Lactation Mastitis"; Vestnik Khirurgi, May 14, 1986, pp. 66-70, and 9 page English translation thereof.
Yusupov. Yu. N., et al; "Active Wound Drainage", Vestnik Khirurgi, vol. 138, Issue 4, 1987, and 7 page English translation thereof.
Davydov, Yu. A., et al; "Bacteriological and Cytological Assessment of Vacuum Therapy for Purulent Wounds"; Vestnik Khirurgi, Oct. 1988, pp. 48-52, and 8 page English translation thereof.
Davydov, Yu. A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.

Chariker, Mark E., M.D., et al; "Effective Management of incisional and cutaneous fistulae with closed suction wound drainage"; Contemporary Surgery, vol. 34, Jun. 1989, pp. 59-63.
Egnell Minor, Instruction Book, First Edition, 300 7502, Feb. 1975, pp. 24.
Egnell Minor: Addition to the Users Manual Concerning Overflow Protection—Concerns all Egnell Pumps, Feb. 3, 1983, p. 1.
Svedman, P.: "Irrigation Treatment of Leg Ulcers", The Lancet, Sep. 3, 1983, pp. 532-534.
Chinn, Steven D. et al.: "Closed Wound Suction Drainage", The Journal of Foot Surgery, vol. 24, No. 1, 1985, pp. 76-81.
Arnljots, Björn et al.: "Irrigation Treatment in Split-Thickness Skin Grafting of Intractable Leg Ulcers", Scand J. Plast Reconstr. Surg., vol. 19, 1985, pp. 211-213.
Svedman, P.: "A Dressing Allowing Continuous Treatment of a Biosurface", IRCS Medical Science: Biomedical Technology, Clinical Medicine, Surgery and Transplantation, vol. 7, 1979, p. 221.
Svedman, P. et al.: "A Dressing System Providing Fluid Supply and Suction Drainage Used for Continuous or Intermittent Irrigation", Annals of Plastic Surgery, vol. 17, No. 2, Aug. 1986, pp. 125-133.
K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.
G. Živadinovic, V. Ðukić, Ž. Maksimović, Ð. Radak, and P. Peška, "Vacuum Therapy in the Treatment of Peripheral Blood Vessels," Timok Medical Journal 11 (1986), pp. 161-164 (certified translation).
F.E. Johnson, "An Improved Technique for Skin Graft Placement Using a Suction Drain," Surgery, Gynecology, and Obstetrics 159 (1984), pp. 584-585.
A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (certified translation).
M. Schein, R. Saadia, J.R. Jamieson, and G.A.G. Decker, "The 'Sandwich Technique' in the Management of the Open Abdomen," British Journal of Surgery 73 (1986), pp. 369-370.
D.E. Tribble, "An Improved Sump Drain-Irrigation Device of Simple Construction," Archives of Surgery 105 (1972) pp. 511-513.
C.E. Tennant, "The Use of Hypermia in the Postoperative Treatment of Lesions of the Extremities and Thorax," Journal of the American Medical Association 64 (1915), pp. 1548-1549.
Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.
V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").
V.A. Kuznetsov & N.A. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").
V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").
V.A.C. ® Therapy Clinical Guidelines: A Reference Source for Clinicians (Jul. 2007).

* cited by examiner

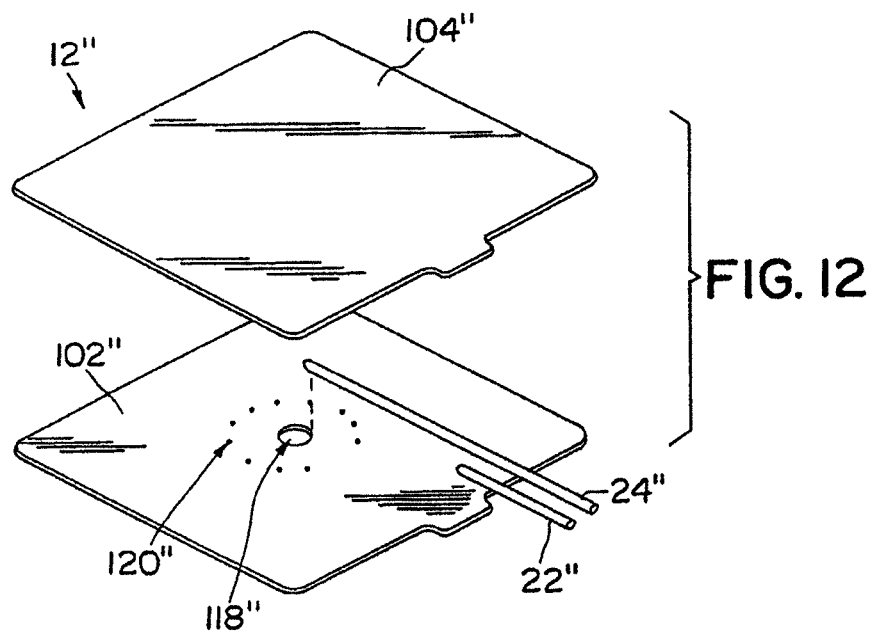
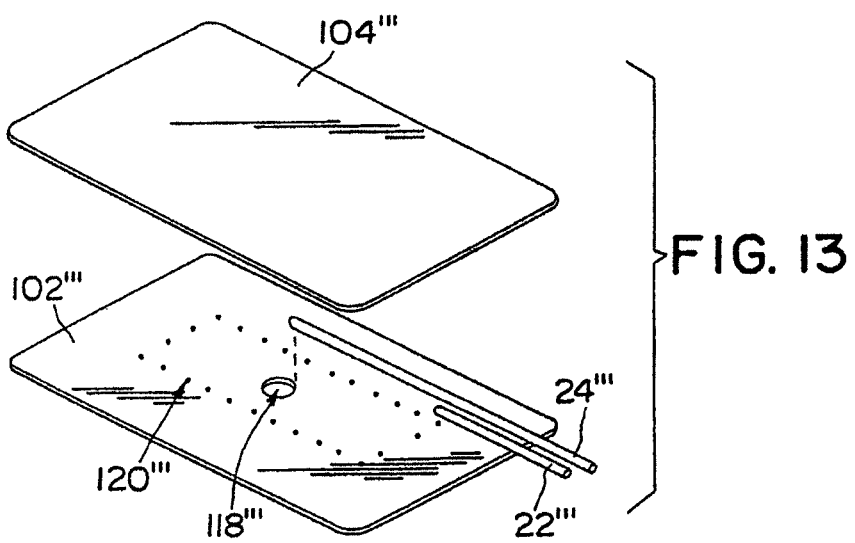

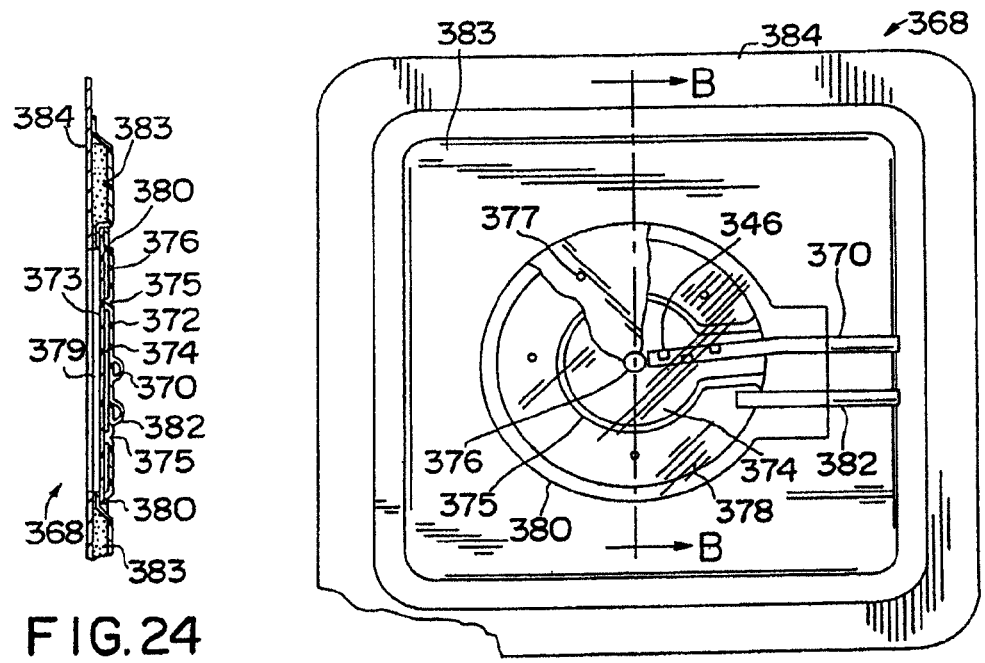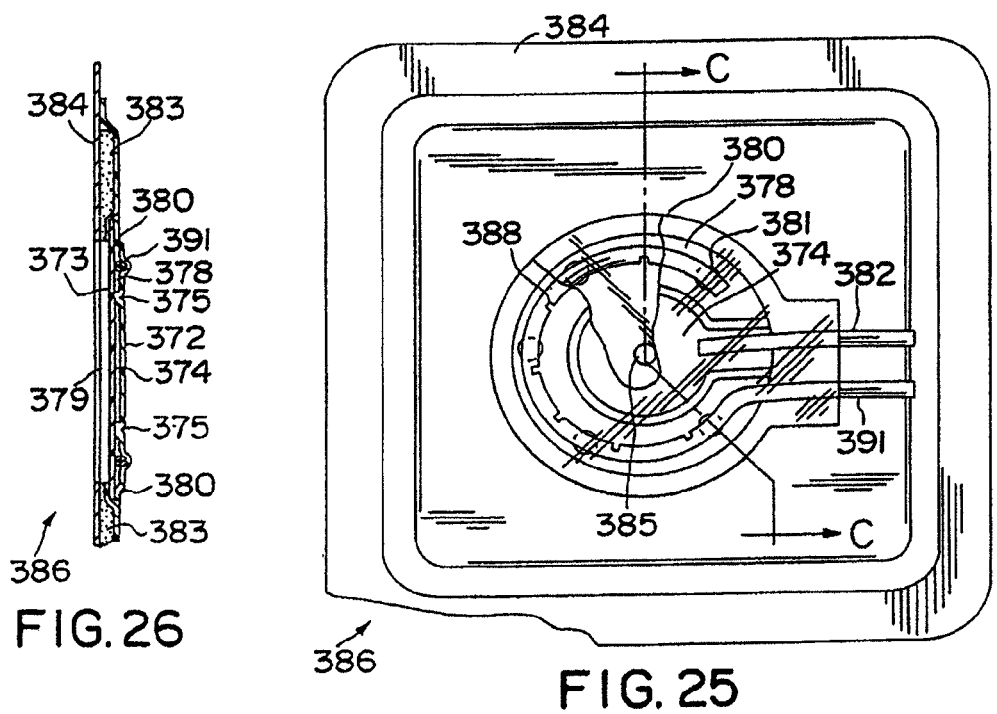

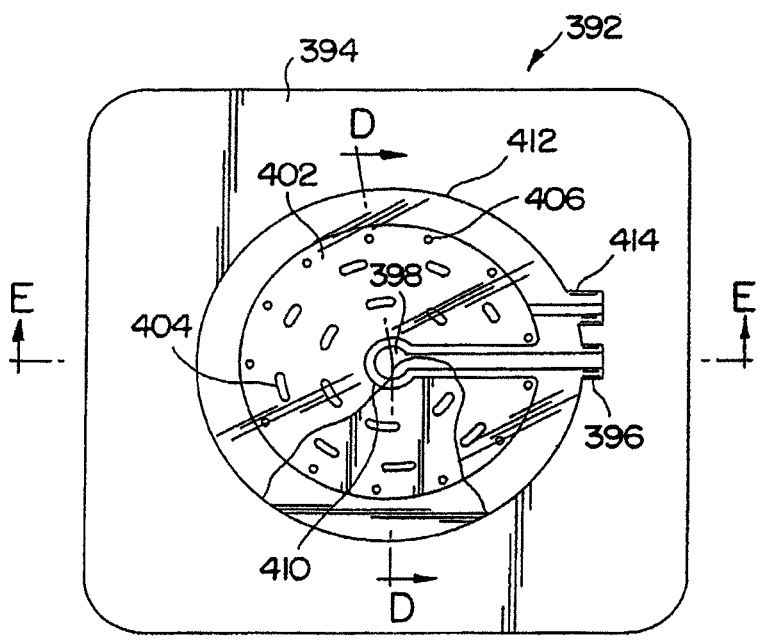
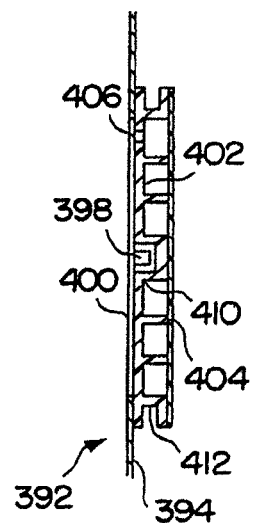
FIG. 27  FIG. 28
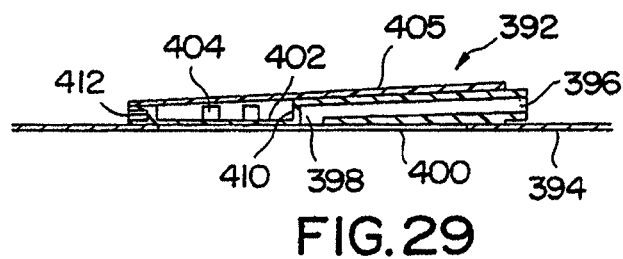
FIG. 29

WOUND TREATMENT APPARATUS

CROSS-REFERENCE TO RELATED APPLICATIONS

This application is a continuation of U.S. application Ser. No. 12/860,581, filed Aug. 20, 2010, which is a divisional application of U.S. patent application Ser. No. 11/761,066, filed Jun. 11, 2007, now U.S. Pat. No. 7,794,438, which is a divisional application of Ser. No. 09/743,737, filed Jan. 16, 2001, now U.S. Pat. No. 7,276,051, which is a U.S. National Counterpart Application of International Patent Application, Serial No. PCT/US99/17877, filed Aug. 6, 1999; which claims priority to U.S. Provisional Patent Application No. 60/095,625, filed Aug. 7, 1998; U.S. patent application Ser. No. 11/761,066 also claims priority to, and is a divisional application of, U.S. patent application Ser. No. 09/369,113, filed Aug. 5, 1999, now U.S. Pat. No. 6,458,109, all of which are hereby expressly incorporated by reference herein.

TECHNICAL FIELD

The present invention relates to a wound treatment apparatus. More particularly, the present invention relates to a wound treatment apparatus for treatment of surface wounds.

BACKGROUND ART

Medical professionals such as nurses and doctors routinely treat patients having surface wounds of varying size, shape, and severity. Variations in wound type and other patient indications dictate variations in desired medications for treatment, such as antibiotics, growth factors, enzymes, hormones, insulin, anesthetics, and the like. The nature of a wound further prescribes variations in treatment protocols, such as delivery rates for medication and temperature control.

It is known that controlling the topical atmosphere adjacent a surface wound can enhance the healing process of the wound, for example by manipulating the oxygen content and/or humidity, or by providing hyperbaric oxygen as part of a treatment protocol, or by introducing medicinal agents adjacent the wound surface. See, for example, Madalene C. Y. Heng, *Topical Hyperbaric Therapy for Problem Skin Wounds,* 19 J. DERMATOL. SURG. ONCOL. 784 (1993); Theodor Kaufman, M. D., et al., *The Microclimate Chamber: The Effect of Continuous Topical Administration of 96% Oxygen and 75% Relative Humidity on the Healing Rate of Experimental Deep Burns,* 23 J. TRAUMA 807 (1983); and U.S. Pat. No. 4,969,881 to Viesturs, entitled "Disposable Hyperbaric Oxygen Dressing." The medical industry would benefit from a practical system for surface wound treatment that provides medical professionals with a flexible way to control the topical atmosphere adjacent the wound, including application of aerosol medications and atmospheric constituents such as oxygen, as well as providing for collection of drainage from the wound site.

Several publications establish that surgeons were active years ago in applying a bandage or cover over a wound to provide a vacuum space above the wound to enhance healing. Nevertheless, Wake Forest University inventors, while not citing the publications, disclosed a vacuum wound therapy in U.S. Pat. Nos. 5,645,081 and 5,636,643.

Conventional treatment of a surface wound typically involves placement of a packing or dressing material, such as cotton gauze, directly in contact with the patient's wound. Often there is a need to change the dressing material frequently because it becomes saturated with effluent material discharged from the wound. The frequency of the need to change the dressing can increase when the care giver applies fluids to the dressing such as a saline solution, peroxide, topical antibiotics, or other medicines dictated by various treatment protocols for different types of wounds.

Changing a wound dressing poses several potential problems for the care giver. Inadvertent contact with sensitive tissue within and adjacent the wound can cause significant discomfort to the patient as well as further trauma to the wound. Exposing the wound to the open atmosphere can increase the chance of infection. Dressings are typically secured in place with adhesives, and thus changing the dressing requires removing the adhesive from the patient's skin, posing risks of pain and trauma to the patient, especially if there is necrotic tissue. Similarly, the dressing material can bind with tissue within the wound, so that changing the dressing can cause tissue loss from the wound, resulting in pain to the patient and retarding the healing process. Medical care givers and patients both would benefit from a bandage system that provides sanitary collection and disposal of material discharged from a wound in the course of the treatment and healing process while reducing the need to remove dressing or packing material placed in contact with the wound.

SUMMARY OF THE INVENTION

According to various features, characteristics, embodiments and alternatives of the present invention which will become apparent as the description thereof proceeds below, the present invention provides a wound treatment apparatus which includes a bandage configured to cover a wound and a seal about the perimeter of the wound. The bandage provides a cavity over the wound with a fluid supply and a fluid drainage in communication with the cavity. This cavity may be maintained at less than atmospheric pressure to enhance healing as known in the prior art. The present invention comprises enhancements to the prior art.

The wound treatment apparatus, for example, includes a first bandage configured to cover a wound. The first bandage includes a first surface configured to face toward the wound, at least one fluid delivery passageway through the first surface, at least one fluid drainage passageway through the first surface and fluid delivery conduit in communication with the fluid delivery passageway. The apparatus also includes a second bandage coupled with the first bandage. The second bandage includes a second surface configured to face toward the first bandage and provide a fluid space between the surfaces and has a fluid drainage conduit in communication with the fluid drainage passageway.

Another embodiment of the wound treatment apparatus includes a bandage including a wound facing surface configured to face toward the wound and a fluid drainage passageway having an opening adjacent the wound facing surface. A fluid drainage tube is coupled to the fluid drainage passageway. First and second fluid drainage receptacles are coupled to the drainage tube. First and second valves are coupled between the fluid drainage tube and the first and second fluid drainage receptacles, respectively.

An additional embodiment of the wound treatment apparatus includes a cover bandage configured to cover a wound and provide a seal on healthy skin tissue about the perimeter of the wound. The cover provides a relatively closed space about the wound which may be held at negative pressure. A fluid supply conduit is fitted between the cover bandage and healthy skin tissue near the wound. A fluid drainage conduit having at least one fluid drainage opening is fitted between the cover bandage and the healthy skin tissue and positioned on healthy skin tissue about the wound and the fluid supply.

A further embodiment of the wound treatment apparatus includes a cover bandage providing a closed seal about a wound and a relatively closed cavity over the wound to be held at a negative pressure. The cover bandage includes a first surface configured to face toward the wound having least one fluid delivery passageway disposed through the first surface, and at least one fluid drainage passageway disposed through the first surface. A second surface is configured to face toward the first surface and provide a fluid space between the surfaces. The fluid space is segregated into a first chamber and a second chamber, wherein the first chamber is formed about the fluid delivery passageway and the second chamber is formed about the fluid drainage passageway. A fluid delivery conduit is in fluid communication with the first chamber and the fluid delivery passageway. A fluid drainage conduit has at least one fluid drainage opening in fluid communication with the second chamber and the fluid drainage passageway.

A still further wound treatment apparatus includes a cover bandage providing a closed seal about a wound positioned on a joint having a cavity over the wound sized to receive the joint and to be held at a negative pressure. The cover bandage includes a first surface configured to face toward the wound, at least one fluid delivery passageway through the first surface, and a second surface configured to face toward the first surface providing a fluid space between the surfaces. A fluid delivery conduit is in fluid communication with the fluid space and the fluid delivery passageway. A fluid drainage conduit having at least one fluid drainage opening is also in fluid communication with the cavity.

Within the present invention, in combination with such a cover bandage, the fluid delivery to the wound may include nebulizers, liquid medication pumps, recirculating temperature regulated fluid tubes, heaters, temperature and pressure sensors, control valves, oxygen supplies, and controllers as described and claimed hereinafter. All of these features, including the vacuum feature, may be programmed to occur on prearranged schedules to deliver care-giver established protocols.

Additional features of the invention will become apparent to those skilled in the art upon consideration of the following detailed description exemplifying the best mode of carrying out the invention as presently perceived.

BRIEF DESCRIPTION OF THE DRAWINGS

The present invention will be described with reference to the attached drawings which are given as non-limiting examples only, in which:

FIG. 12 is a perspective view of another alternative embodiment of a bandage assembly;

FIG. 13 is a perspective view of yet another alternative embodiment of a bandage assembly;

FIG. 23 is a top view of a wound treatment assembly including another embodiment of the present invention;

FIG. 24 is a sectional view of the wound treatment assembly from FIG. 23, taken along line B-B;

FIG. 25 is a top view of a wound treatment assembly in accordance with a still further embodiment of the present invention;

FIG. 26 is a sectional view of the wound treatment assembly from FIG. 25, taken along line C-C;

FIG. 27 is a top view of a wound treatment assembly in accordance with an additional embodiment of the present invention;

FIG. 28 is a sectional view of the wound treatment assembly from FIG. 27, taken along line D-D;

FIG. 29 is a sectional view of the wound treatment assembly from FIG. 27, taken along line E-E;

DETAILED DESCRIPTION OF DRAWINGS

Figure 1:
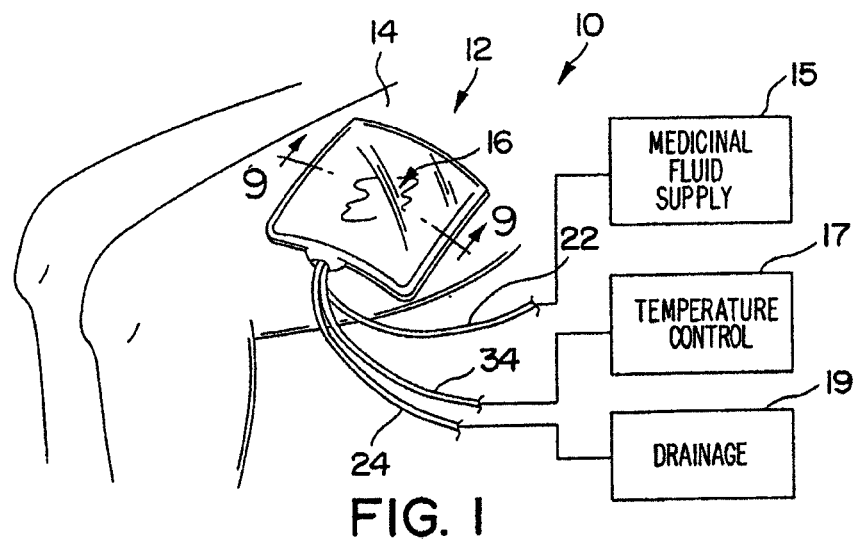
FIG. 1 is a perspective view of a wound treatment apparatus according to the present invention.

Referring now to the drawings, FIG. 1 illustrates a wound treatment apparatus 10 that includes a bandage assembly 12 coupled to a patient's skin 14 adjacent a surface wound 16. Apparatus 10 includes a wound temperature control system 17, a wound drainage system 19, and a medicinal fluid supply system 15 including a nebulizer 26 shown in FIGS. 2 and 3. Wound treatment apparatus 10 provides a system for controlling the topical atmosphere adjacent wound 16, including delivery of medication, control of atmospheric constituents, temperature regulation, and collection of wound drainage.

Including a nebulizer 26 (see FIGS. 2 and 3) in wound treatment apparatus 10 provides for delivering nebulized fluid containing dissolved wound treatment constituents, such as oxygen or medication, to the wound. As a wound heals it develops a liquid layer on its external surface. This liquid layer forms a barrier that impedes flow of atmospheric constituents, such as oxygen or medication, to the cells in the wound, because these constituents must diffuse through the liquid layer. Application of nebulized fluid improves treatment and healing because the nebulized fluid can readily mix with the liquid layer. This allows the dissolved constituents in the nebulized fluid to be readily diffused through the liquid layer and absorbed into the cells below.

Bandage assembly 12 is a two-part assembly that includes a fluid medication delivery bandage 18 and an adsorbent drainage bandage 20. Drainage bandage 20 is configured to be removably coupled to delivery bandage 18 as shown, for example, in FIGS. 2 and 3. Delivery bandage 18 provides for sealing the wound site from the ambient atmosphere so that supply system 15, temperature control system 17, and drainage system 19 can regulate the wound environment. By providing a two-piece, removably coupled bandage arrangement, bandage assembly 12 allows for changing the drainage bandage without the need to remove delivery bandage 18 from the patient's skin 14.

Delivery bandage 18 includes a medicinal fluid supply tube 22 and is coupled to the patient's skin 14 over wound 16. Delivery bandage 18 can remain in place while drainage bandage 20 can be changed as needed during wound treatment. Drainage bandage 20 includes a wound drainage tube 24 that is coupled to wound 16 through delivery bandage 18 to allow fluid from wound 16 to exit from bandage assembly 12, the fluid including both fluids secreted by wound 16 as well as fluids entering bandage 18 through medicinal fluid supply tube 22. Bandage assembly 12 thus allows control of the topical atmosphere adjacent wound 16 while limiting the exposure to atmospheric contaminants, allowing for use of treatment protocols to enhance healing while reducing opportunities for potential infection and trauma.

Figure 2:
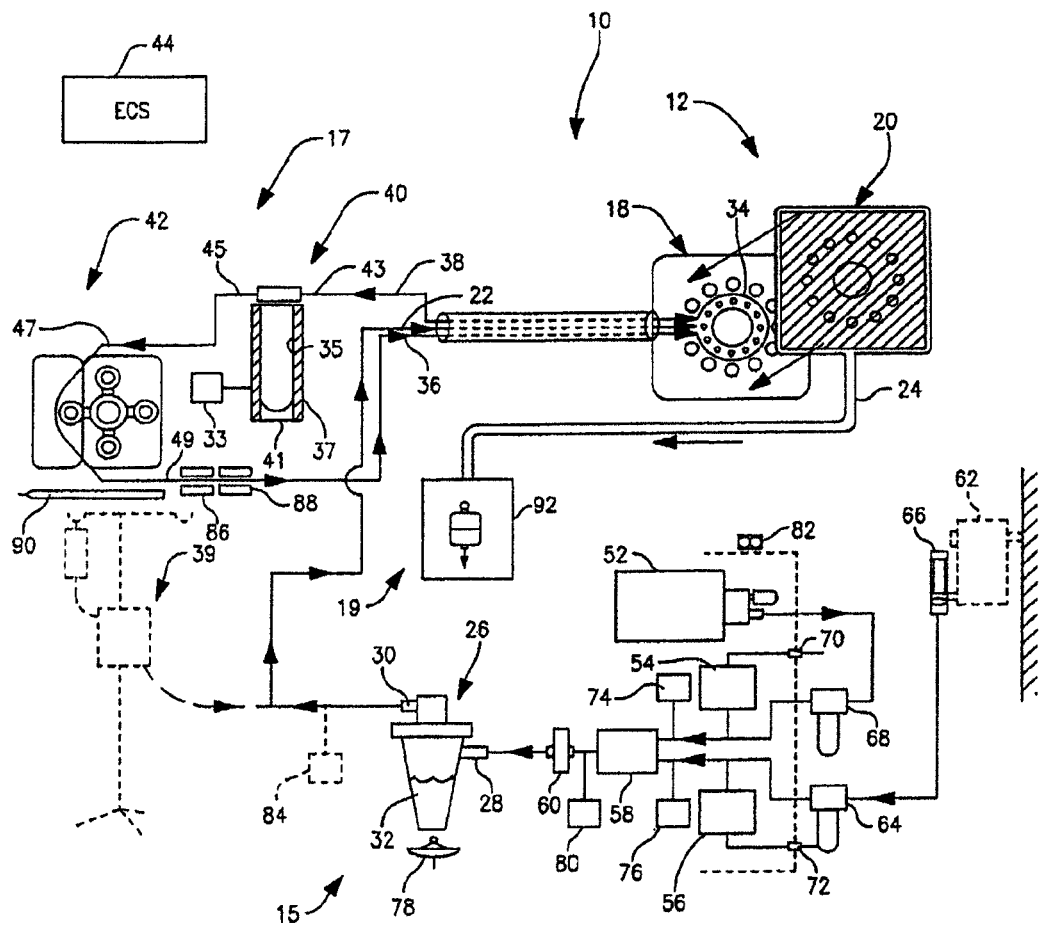
FIG. 2 is a schematic block diagram of a wound treatment apparatus according to the present invention.
Figure 3:
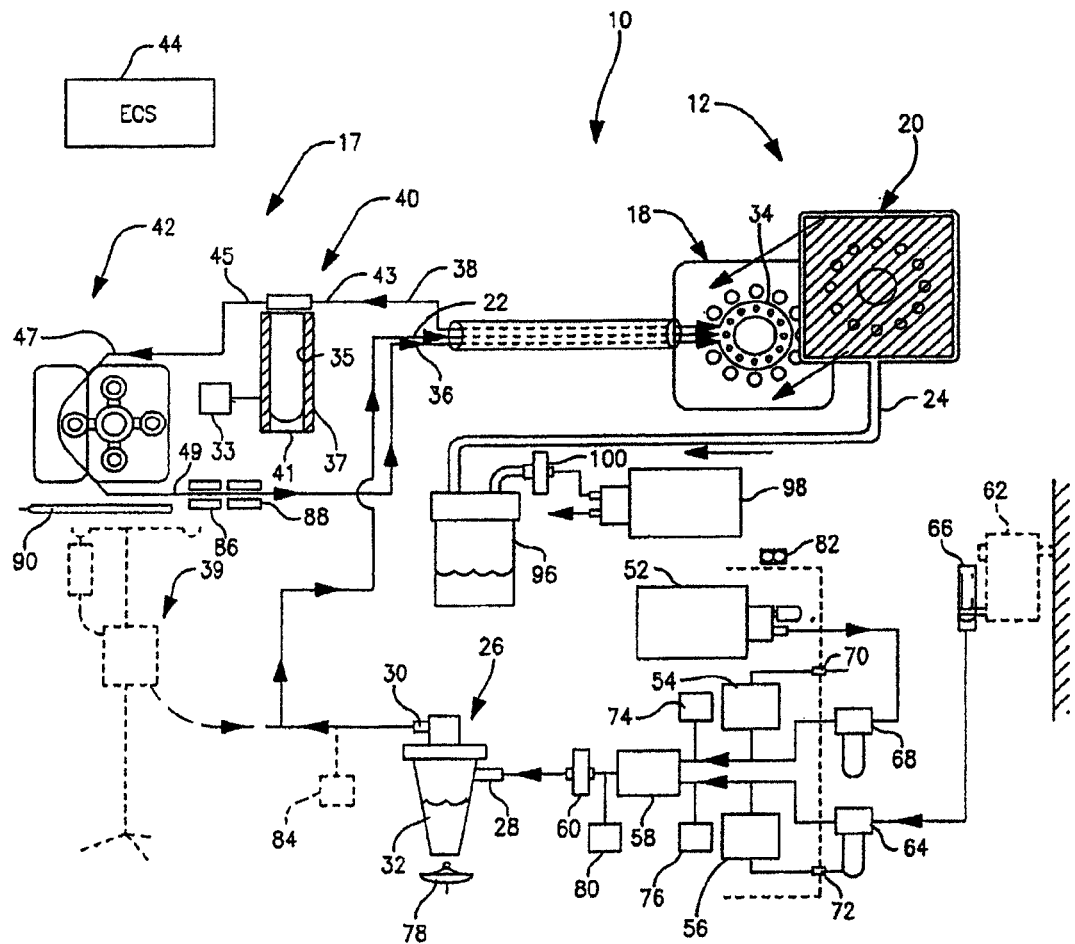
FIG. 3 is a schematic block diagram of an alternative embodiment wound treatment apparatus.

Medicinal fluid supply system 15 of wound treatment apparatus 10 illustratively includes nebulizer 26 and an optional liquid medication pump 39 as shown in FIGS. 2 and 3. Temperature control system 17 includes a heater 40 and pump 42. Drainage system 19 includes a drainage bag 92 as shown in FIG. 2 or alternatively a vacuum pump 98 and liquid trap bottle 96 as shown by 19' in FIG. 3.

Nebulizer 26 includes an input port 28 for accepting a nebulizer gas input, such as standard air or pure oxygen, a nebulized fluid output port 30, and a liquid reservoir 32 coupled between input and output ports 28, 30. Liquid reservoir 32 illustratively contains medication as needed to implement a treatment protocol for wound 16, such as antibiotics, growth factors, enzymes, hormones, insulin, anesthetics, and the like. It is understood that reservoir 32 can contain any fluid, such as pure water or a saline solution. Nebulizer 26 is illustratively a Mini Heart model manufactured by Vortran, which can atomize approximately 4 milliliters per hour of liquid medication at an input gas flow rate of approximately 1.5 liters per minute. It is understood, however, that any suitable nebulizing device can be used.

Nebulizer output port 30 is coupled to medicinal fluid supply tube 22 of delivery bandage 18 of bandage assembly 12. Optionally, a liquid medication pump 39 such as an IV pump can also be coupled to medicinal fluid supply tube 22.

Wound treatment apparatus 10 thus provides for delivery of either aerosol or liquid medication or both to wound 16 through delivery bandage 18.

As discussed in more detail below, delivery bandage 18 further includes a recirculating fluid tube 34 having an input port 36 and an output port 38. Wound treatment apparatus 10 includes a heater 40 and a peristaltic pump 42 coupled between the input and output ports 36, 38 of recirculating fluid tube 34. Temperature control system 17 thus allows temperature controlled liquid to flow through bandage assembly 12 to regulate the temperature at the site of wound 16.

Peristaltic pump 42 is illustratively a Model 313 manufactured by Watson Marlow, using a nominal flow rate of between 200 to 250 milliliters per minute. Although a peristaltic pump driven by an AC synchronous motor at 72 RPM is used because its disposable tubing elements eliminate the need to clean the pump between patient uses, it is understood that other pump designs such as centrifugal, gear-driven, or diaphragm type pumps can be used.

Heater 40 illustratively is a specially designed tubular unit that includes a tubular housing 37, a 100 watt heater element 35 positioned within housing 37, and a thermocouple 33 for monitoring the temperature of heater element 35. A fluid reservoir 41 is configured to fit within housing 37 so that heater element 35 can heat the recirculating fluid. As discussed below, other suitable heating systems can be used.

Fluid reservoir 41 illustratively is formed from a rubber silicone tube configured to fit snugly within housing 37. Reservoir 41 advantageously is provided as a prepackaged unit with bandage assembly 12 along with associated tubes to prevent spillage that can accidentally occur if an open container is used for the recirculating fluid. It is understood, however, that other suitable devices for controlling the temperature of the recirculating fluid can be used, such as an immersion heater configured to be placed within an open fluid reservoir (not shown), or alternative embodiment heating assembly 200 as shown in FIGS. 14-18 and discussed in detail below.

Wound treatment apparatus 10 further includes a computer-based electronic control system 44 that is coupled electronically to the electronic and electro-mechanical components such as nebulizer 26, peristaltic pump 42, heater 40 and thermocouple 33. Control system 44 provides for automated control of wound treatment apparatus 10 for various treatment protocols, for example to regulate temperature at the wound site by using heater 40 and pump 42 to regulate recirculating fluid temperature to 37° Celsius.

Control system 44 illustratively is directly coupled to the controlled components using analog, discrete, and serial I/O signals as required by the various component interfaces. It is understood that the communication mechanism can include any type of electronic network, such as any serial bus or parallel bus architecture. The communications protocol similarly can vary. For example, master-slave, token ring, or peer-to-peer communication protocols, such as Ethernet or Echelon LONworks™, can be used. By providing software control of wound treatment apparatus 10 components such as nebulizer 26, heater 40, and pump 42, control system 44 can automatically control the delivery of aerosol medication, temperature, and oxygen concentration levels at the site of wound 16 to implement a desired treatment protocol and to provide an optimal wound healing environment.

Nebulizer input port 28 is coupled to a nebulizer gas input assembly 46 that includes air and oxygen input ports 48, 50, an air compressor 52, air and oxygen pressure regulators 54, 56, a selector valve 58, and a nebulizer gas input filter 60. Filter 60 is illustratively a single use disposable bacteria filter.

Oxygen input port 50 can illustratively be coupled to a standard hospital oxygen blender 62 through a standard hospital air filter and water trap 64. An internal compressed oxygen supply (not shown) can replace oxygen blender 62. Oxygen filter and water trap 64 contains a 5 micron filter element and catch basin to trap particulate matter and condensed water output from oxygen blender 62. Blender 62 further illustratively includes an oxygen flowmeter 66 such as a standard hospital is pediatric flowmeter that allows a flow set range of, for example, between zero and three liters per minute.

Air compressor 52 is coupled to nebulizer air input port 48 through an external air filter and water trap 68. Similar to supply of oxygen, an external compressed air supply (not shown) can also be used. Air compressor 52 is illustratively a diaphragm type pump driven by a brushless DC motor that can deliver a minimum of 1.3 liters per minute at 15 psi. Compressor 52 includes an input filter (not shown) having a 25 micron filter/silencer. Similar to oxygen filter and water trap 64, air filter and water trap 68 contains a 5 micron filter element and catch basin for trapping particulate matter and water droplets from the compressed air output from compressor 52.

Air and oxygen input ports 48, 50 are coupled to selector valve 58 through air and oxygen pressure regulators 54, 56, respectively. Regulators 54, 56 maintain air and oxygen pressure between about 15 and about 17 psi. Air pressure regulator 54 vents excess air outside of wound treatment apparatus 10 through an air vent 70 and oxygen pressure regulator vents through oxygen vent 72.

Selector valve 58 is coupled electronically to control system 44 to allow for software control of the mixing of air and oxygen so that the gas input to nebulizer 26 can range from pure air to pure oxygen. Selector valve 58 can eliminate the need for external oxygen blender 62. Selector valve 58 illustratively switches between air and oxygen at a predetermined rate, although other valve arrangements can be used to mix air and gas, such as a dual input mixing valve, a pair of butterfly valves or other valve configurations for mixing two fluid input streams. Control system 44 can be used to supply an air/oxygen treatment protocol to the wound site automatically. For instance, control system 44 can implement a programmed protocol to deliver 3 hours of air followed by 3 hours of oxygen, and so on, to the wound site. Valve 58 automatically switches to implement the programmed protocol.

Nebulizer gas input assembly 46 further includes an air pressure sensor 74 coupled between selector valve 58 and air pressure regulator 54, an oxygen pressure sensor 76 coupled between selector valve 58 and oxygen pressure regulator 56, and a nebulizer gas input pressure sensor 80 coupled between selector valve 58 and nebulizer input port 28. Sensors 74, 76, 80 are coupled to control system 44 to provide feedback for monitoring of proper system operation and so that an alarm can be indicated and wound treatment apparatus 10 shut down automatically if a pressure signal exceeds a predetermined threshold.

Wound treatment apparatus 10 also includes a nebulizer empty sensor 78 to indicate if nebulizer 26 is empty. Nebulizer empty sensor 78 provides a feedback signal to electronic control system 44 and illustratively is an acoustical sensor. Control system 44 continuously monitors the output signal from sensor 78, which changes distinctively when reservoir 32 becomes empty, at which point an alarm can be signaled and wound treatment apparatus 10 shut down. It is understood that other types of sensors can be used to determine if nebulizer 26 is empty, such as, for example, capacitive sensors, float switches, or optical, infrared, or ultrasonic sensors.

Wound treatment apparatus 10 further includes a nebulizer pressure sensor 80 coupled between selector valve 58 and nebulizer input port 28. Pressure sensor 80 provides a feedback signal to control system 44 indicative of pressure within nebulizer 26 and is also used to verify the proper operation of selector valve 58. Wound treatment apparatus 10 furthermore includes a tilt sensor 82 and a bandage interface pressure sensor 84, both coupled to control system 44. Tilt sensor 82 signals an alarm and shuts down apparatus 10 if apparatus 10 is tilted beyond a predetermined threshold, illustratively 30°.

Bandage interface pressure sensor 84 is coupled between nebulizer output port 30 and medicinal fluid supply tube 22 of bandage assembly 12. By monitoring back pressure from the bandage, pressure sensor 84 allows control system 44 to provide a display indicative of pressure at the interface between delivery bandage 18 or between the patient and a bed when the patient is lying directly on bandage assembly 12. Control system 44 can also signal an alarm and shut down apparatus 10 if interface pressure exceeds a predetermined threshold.

Pressure on a wound can cause further skin breakdown, especially if the wound is a decubitus ulcer or bed sore. The wound interface pressure from sensor 84 can be used as a feedback signal to a bed control or a support surface control to adjust a therapy surface. Sensor output 84 can also signal the care giver through the control system and a nurse call system so that the care-giver can move the patient, either on the existing mattress or to a reduced pressure support surface, for treating the wound.

Temperature control system 17 includes heater 40, reservoir 41, and pump 42. Fluid reservoir 41 includes an input port 43 coupled to output port 38 of recirculating fluid tube 34 and an output port 45 coupled to a tube feeding peristaltic pump 42.

Peristaltic pump 42 includes a pump input port 47 coupled to reservoir output port 45 and a pump output port 49 coupled to input port 36 of recirculating fluid tube 34. A pump output temperature sensor 86 and a pump safety shutoff temperature sensor 88 both are coupled between pump port 49 and recirculating fluid input port 36 of bandage assembly 12.

Pump output temperature sensor 86 provides a feedback to control system 44 for closed loop control of heater 40 to control fluid input temperature to tube 34 in bandage assembly 12 to a desired temperature, illustratively 37° Celsius. Safety shutoff temperature sensor 88 is similarly provided as a feedback to control system 44 and is used to disable and alarm apparatus 10 if recirculating fluid temperature exceeds a safe limit, such as 41° Celsius. Sensors 86, 88 illustratively are non-contact, infrared sensors such as an IRt/c.01HB-J-37C sensor from Exergen Corp., although it is understood that other suitable sensors can be used.

Optionally, proximity sensors (not shown) can be used to ensure that temperature sensors 86, 88 are properly coupled. For example, temperature sensors 86, 88 and respective proximity sensors can be coupled to a housing or channel into which a tube from recirculating fluid supply input port 36 is installed. If the proximity sensors do not detect the tube's presence within the channel, control system 44 can react accordingly, such as by providing a suitable display and/or alarm and/or by shutting down the system.

Temperature control system 17 further includes a liquid leak sensor 90 coupled adjacent pump 42 to monitor leaks from pump 42 or adjacent tubing. Sensor 90 is illustratively a capacitive sensor pad located under peristaltic pump 42. Sensor 90 provides a signal to electronic control system 44, which can alarm and disable wound treatment apparatus 10 if a leak is detected.

Wound treatment apparatus 10 further includes a wound effluent drainage receptacle or bag 92 that collects fluid flowing from bandage assembly 12 out of drainage tube 24, including both fluid supplied into bandage assembly 12 from supply tube 22 and discharge from wound 16. Drainage bag 92 includes a vapor filter 94 to filter gaseous components of fluid exiting bandage assembly 12. Vapor filter 94 is illustratively a standard hospital ventilator exhaust filter configured to plug directly into the side of drainage bag 92.

An alternative embodiment wound treatment apparatus 10' is shown in FIG. 3. Apparatus 10' replaces wound effluent drainage bag 92 and vapor filter 94 of apparatus 10 with a liquid trap bottle 96, a vacuum pump 98, and a vacuum filter 100 coupled between trap bottle 96 and pump 98. Liquid trap bottle 96 is coupled to drainage tube 24 to collect liquids in the fluid flow from bandage assembly 12. Vacuum pump 98 is used to apply a negative pressure to facilitate drainage. If desired, sufficient negative pressure can be applied so that negative pressure on the wound facilitates its closure. Filter 100 illustratively is a hydrophobic bacteria filter coupled between trap bottle 96 and vacuum pump 98.

Referring now to FIGS. 4-10, bandage assembly 12 includes delivery bandage 18 and drainage bandage 20. Delivery bandage 18 includes bottom and top sheets 102, 104 that sandwich both medicinal fluid supply tube 22 and recirculating fluid tube 34. Drainage bandage 20 includes bottom and top sheets 106, 108 that sandwich an adsorbent pad 110 and drainage tube 24. Adsorbent pad 110 is illustratively formed from medical grade hydrophilic foam, although any suitable material such as an absorbent substance can be used. Bandage sheets 102, 104, 106, 108 are illustratively formed from clear, flexible polyurethane or vinyl that meets USP Class VI requirements for medical applications.

Figure 5:
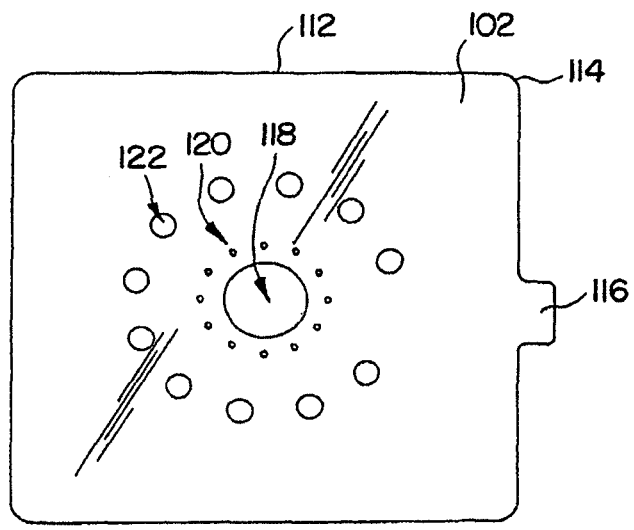
FIG. 5 is a top view of the bottom sheet of the medicinal delivery bandage of FIG. 4.

Delivery bandage bottom sheet 102 is formed with a generally square perimeter 112 having rounded corners 114 and a tab 116 along a side of perimeter 112 as best shown in FIG. 5. Bottom sheet 102 further includes a central wound drainage passageway 118, a plurality of medicinal fluid supply passageways 120 arranged in a circular pattern concentric with passageway 118, and a plurality of outer wound drainage passageways 122 arranged in another concentric circular pattern radially outward of delivery passageways 120. Delivery passageways 120 provide for delivery of fluid medications from medicinal fluid supply tube 22 to wound 16 and illustratively are relatively smaller than drainage passageways 118, 122 that provide for passage of wound drainage through delivery bandage 18.

Figure 6:
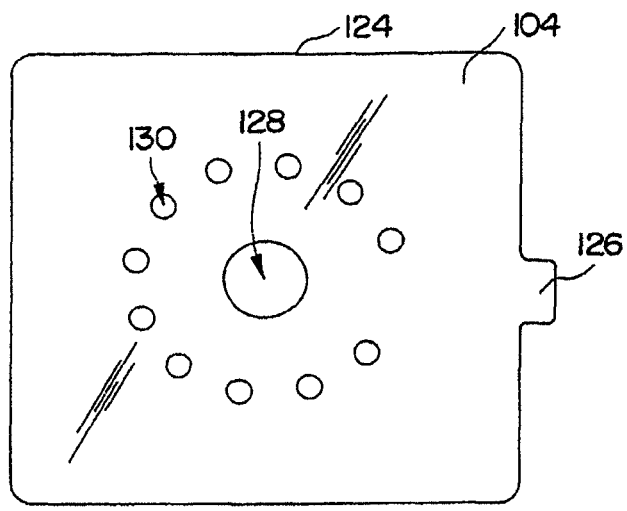
FIG. 6 is a top view of the top sheet of the medicinal delivery bandage of FIG. 4.

Delivery bandage top sheet 104 is formed to include a perimeter 124, tab 126, central passageway 128, and outer passageways 130 that are configured to align with perimeter 112, tab 116, central passageway 118, and outer passageways 122 of bottom sheet 102 as best shown in FIG. 6. When top and bottom sheets 102, 104 are aligned, central passageways 118, 128 and outer passageways 122, 130 are in fluid communication and allow wound effluent to pass through bandage 18.

Figure 7:
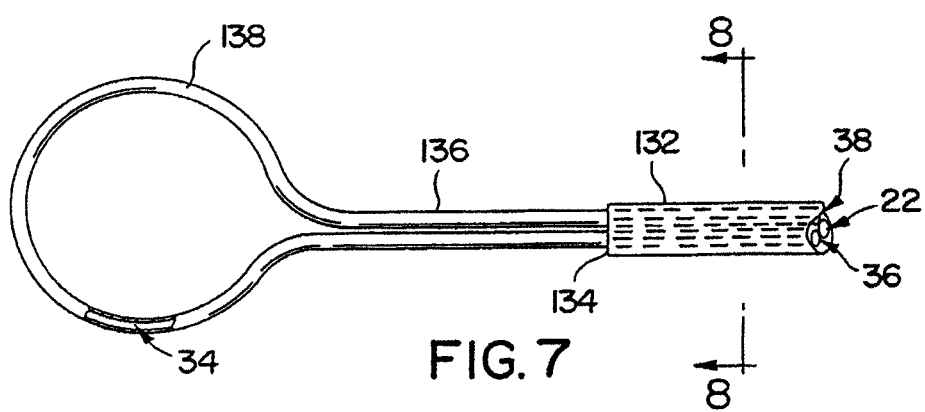
FIG. 7 is a top view of the medicinal fluid supply and temperature controlled, recirculating fluid tubes of FIG. 4.
Figure 8:
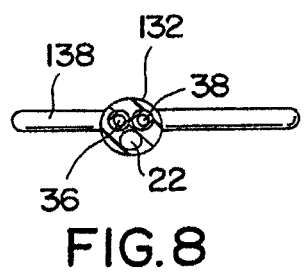
FIG. 8 is an end view of the medicinal fluid supply and temperature controlled, recirculating fluid tubes of FIG. 7.

Medicinal fluid supply tube 22 and recirculating fluid tube 34 illustratively are contained within a multi-lumen tube 132 as best shown in FIGS. 7 and 8. It is understood that separate tubes can be used. Multi-lumen tube 132 is a 65 durometer USP Class VI polyvinyl chloride triple lumen tube and has three channels, one of which defines supply tube 22 and the other two define portions of recirculating fluid tube 34. Tube 132 includes a terminal end 134 that defines an end of medicinal fluid supply tube 22.

Recirculating fluid tube 34 further includes a straight segment 136 that extends axially outward from end 134 and a generally circular segment 138 coupled to straight segment 136 as best shown in FIG. 7. The geometry of recirculating fluid tube 34 can vary as needed to distribute temperature controlled fluid throughout delivery bandage 18. Temperature regulated fluid, illustratively water, is circulated through delivery bandage 18 in segments 136, 138 from temperature control system 17 to maintain bandage 18 at an optimal temperature for wound treatment. It is understood that the temperature of bandage 18 can be regulated by control system 44 according to a desired treatment protocol, for example by maintaining a temperature to maximize treatment effectiveness of an enzyme or other medicinal fluid supplied through medicinal fluid supply tube 22.

Figure 10:
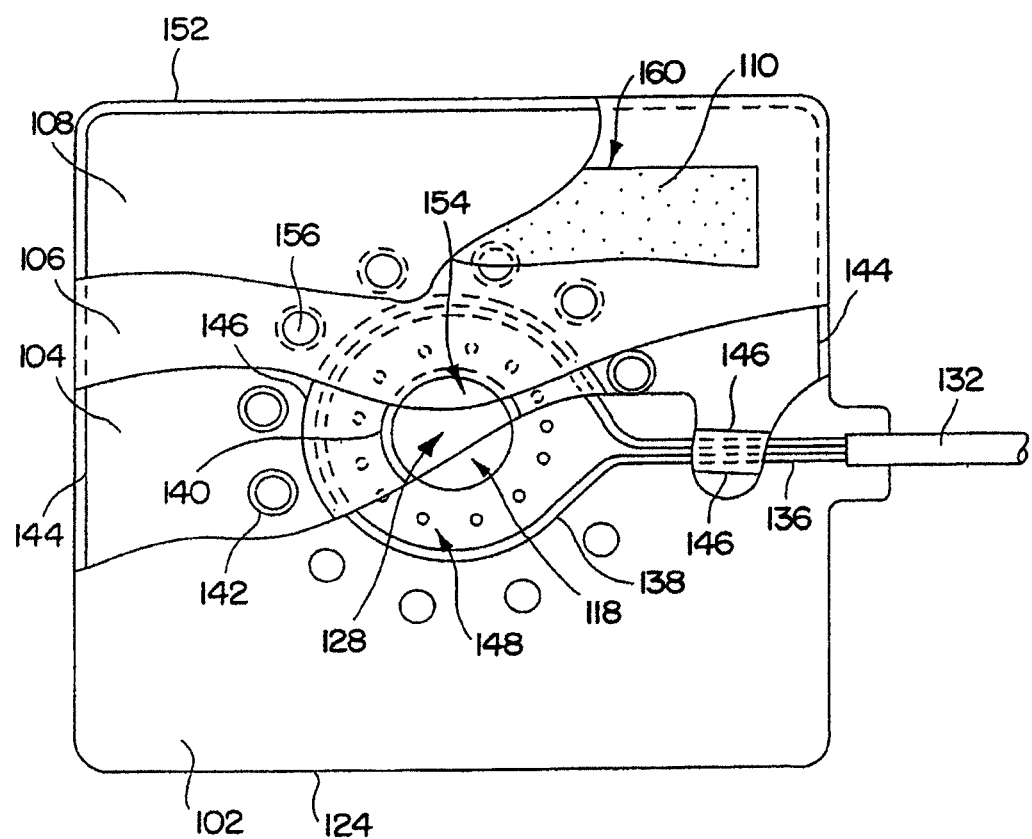
FIG. 10 is a top view of the bandage assembly of FIG. 1 with portions broken away.

Delivery bandage 18 is formed by sandwiching multi-lumen tube 132 between top and bottom sheets 102, 104 so that tube 132 extends over tabs 116, 126 and circular segment 138 is concentric with central passageways 118, 128 as best shown in FIG. 10. Top and bottom sheets 102, 104 are bonded together by radio frequency (RF) welding. Circular RF welds 140, 142 seal the perimeter around each pair of aligned wound drainage passageways 118, 128, and 122, 130. A perimeter RF weld 144 seals the aligned perimeters 112, 124.

A fluid delivery chamber weld 146 extends from perimeter weld 144 and encompasses inner wound drainage passageway weld 140 to define a fluid delivery chamber 148 that is in fluid communication with delivery passageways 120 in bottom sheet 102 and terminal end 134 of medicinal fluid supply tube 22. Thus, aerosol or liquid medications supplied through medicinal fluid supply tube 22 from nebulizer 26 or medicinal pump 39 can be delivered through delivery bandage 18 to wound 16 through chamber 148 that is isolated from wound drainage passageways 118, 122, 128, 130. Recirculating fluid tube 34 illustratively is contained within delivery chamber 148, although it is understood that tube 34 could be isolated from chamber 148.

Figure 4:
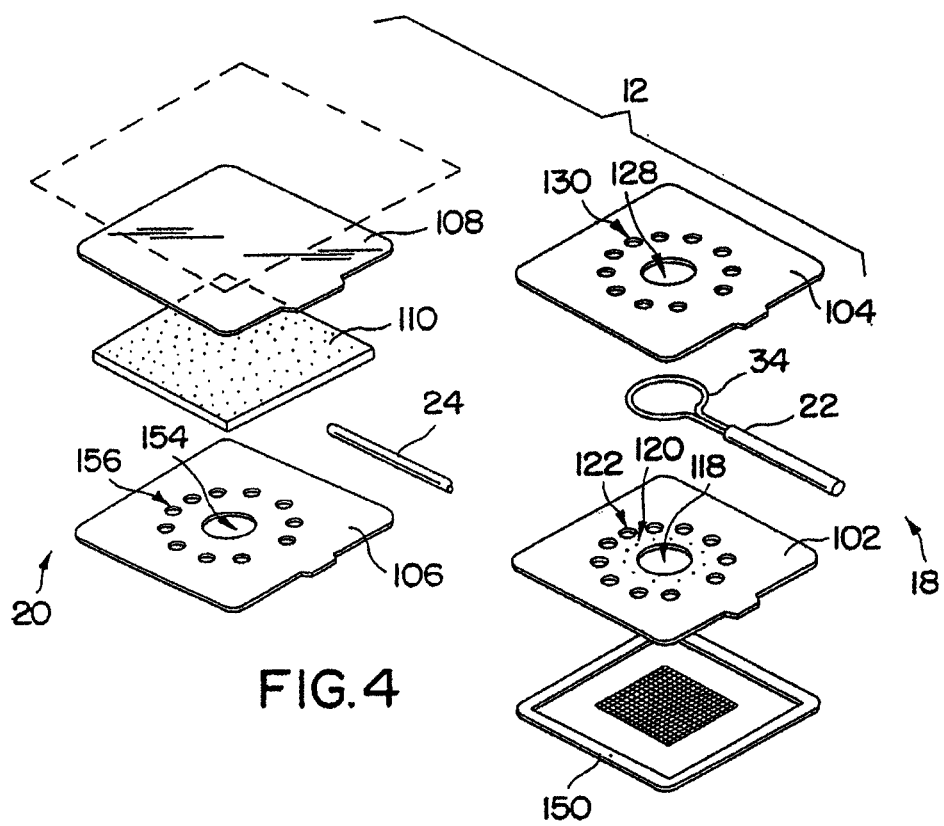
FIG. 4 is an exploded perspective view of a two-piece bandage assembly according to the present invention.
Figure 9:
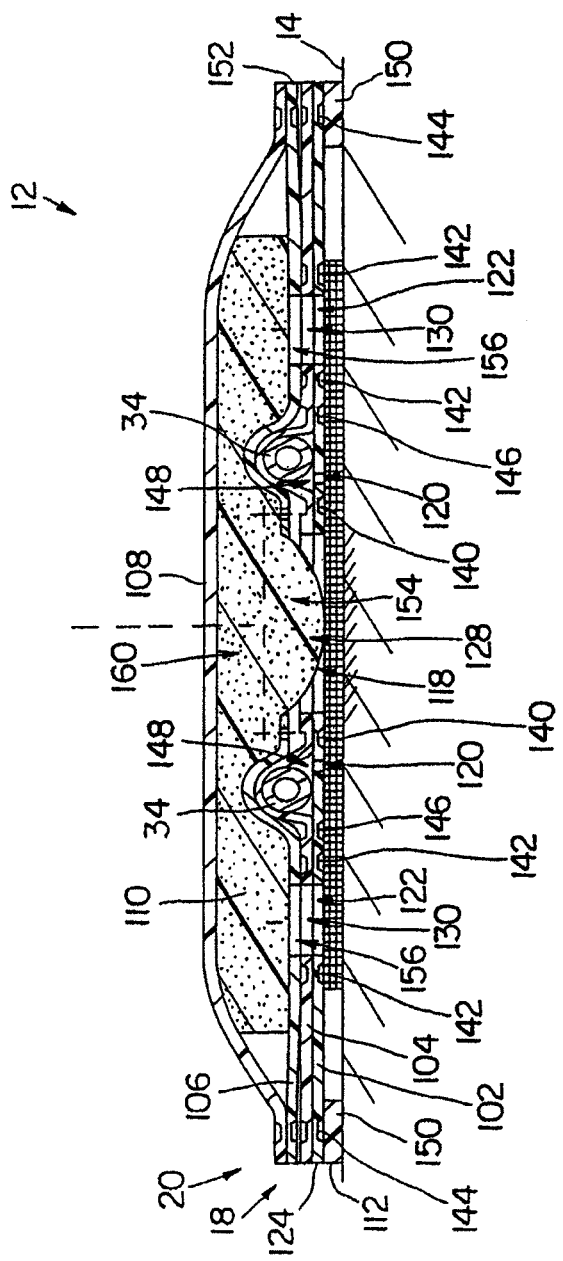
FIG. 9 is a sectional view taken along line 9-9 of FIG. 1.

Delivery bandage 18 further includes a sealing gasket 150 coupled to bottom sheet 102 adjacent its perimeter 112 as shown in FIGS. 4 and 9. Gasket 150 is illustratively a thin foam frame that includes an adhesive coating for coupling gasket 150 both to bottom sheet 102 and for removably coupling gasket 150 to a patient's skin 14. Gasket 150 provides an improved seal between bottom sheet 102 of delivery bandage 18 and skin 14 to allow wound treatment apparatus 10 to control the topical atmosphere adjacent wound 16. It is understood that other suitable materials can be used to provide a gasket, such as an appropriate layer of adhesive material.

Bottom sheet 106 of drainage bandage 20 includes a perimeter 152, central drainage passageway 154, and outer drainage passageways 156 that are configured to align with the corresponding perimeter 124 and passageways 128, 130 of top sheet 104 of delivery bandage 18. Bottom sheet 106 includes a thin layer of adhesive 158 formed as an open frame adjacent perimeter 152 to provide for removably coupling to delivery bandage top sheet 104. Adhesive 158 is configured to remain on bottom sheet 106 of drainage bandage 20 after uncoupling to allow for easy replacement of drainage bandage 20 without the need to remove delivery bandage 18.

Top sheet 108 of drainage bandage 20 has no passageways and is configured to align with bottom sheet 106 to provide a cavity 160 that receives adsorbent pad 110. Drainage bandage 20 is formed by sandwiching drainage tube 24 between top and bottom sheets 106, 108, which are then sealed together by RF welding adjacent their perimeters. Drainage bandage 20 thus channels wound effluent from delivery bandage 18, through pad 110, and out drainage tube 24 in an assembly that is easily replaceable, for example when adsorbent pad 110 becomes saturated or otherwise contaminated.

Bandage assembly 12 thus provides a two-piece bandage in which drainage bandage 20 can be removed and replaced while leaving delivery bandage 18 in situ. Drainage passageways 118, 122, 128, 130 thus allow for access to wound 16 through delivery bandage 18 when drainage bandage 20 is removed. Thus, a medical care giver can take a culture or sample from wound 16 without the need to remove delivery bandage 18.

Figure 11:
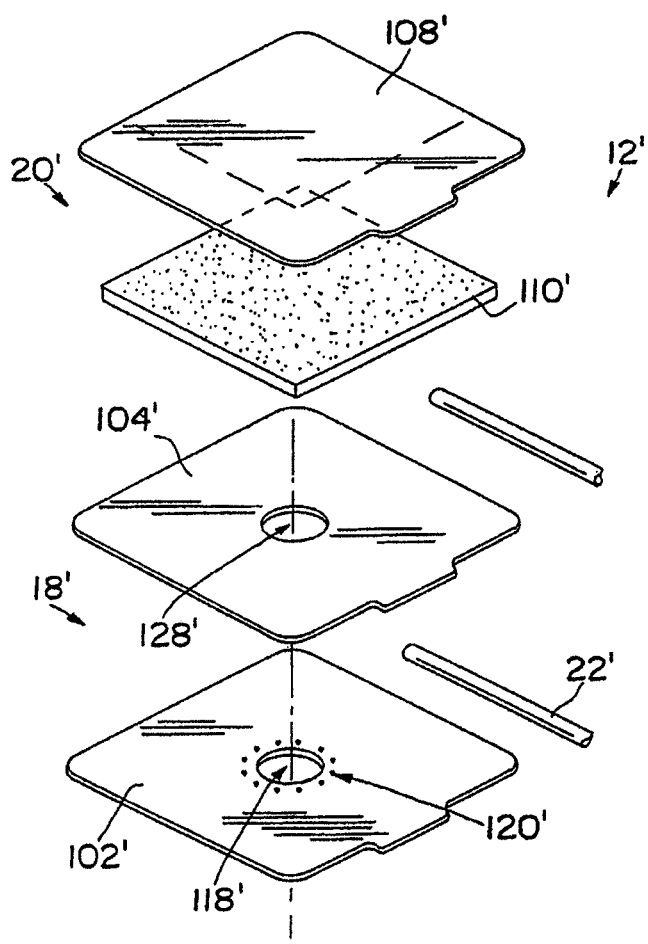
FIG. 11 is an exploded perspective view of an alternative embodiment of a bandage assembly.

An alternative embodiment bandage assembly 12' includes a one-piece combination delivery and drainage bandage comprising a delivery bandage portion 18' and drainage bandage portion 20' as shown in FIG. 11. Delivery bandage portion 18' includes a bottom sheet 102' that has a single drainage passageway 118' and a plurality of medicinal fluid delivery passageways 120'. Top sheet 104' includes a single drainage passageway 128'. Delivery bandage portion 18' includes a medicinal fluid supply tube 22' for use as discussed above in providing nebulized or liquid medication, etc. Drainage bandage portion 20' includes a pad 110', a top sheet 108', and a drainage tube 24'. Drainage tube 24' is coupled to bandage assembly 12' between sheets 104' and 108'.

Another alternative bandage assembly 12" is formed with only top and bottom sheets 102", 104" as shown in FIG. 12. Bottom sheet 102" includes a central drainage passageway 118" and a plurality of delivery passageways 120" arranged in a circular pattern radially outward of drainage passageway 118". A medicinal fluid supply tube 22" and a drainage tube 24" are coupled between top and bottom sheets 102", 104", with radio frequency welds (not shown) isolating the delivery tube and passageways 22", 120" from drainage tube 22" and passageway 118".

Yet another alternative bandage assembly 12''' is formed with elongated top and bottom sheets 102''', 104''' as shown in FIG. 13. Delivery passageways 118''' are arranged in a rectangular pattern to provide for delivery of fluid medication and control of the topical atmosphere adjacent a surface wound 16 having an elongated shape. Drainage passageway 120''' is illustratively circular, although drainage passageway 120''' can be formed in any suitable shape, such as an elongated rectangular or elliptical opening. Embodiment 12''' illustrates how bandages according to the present invention can readily be adapted for treatment of any wound shape by suitable geometric adaptations of the bandage assembly.

Figure 14:
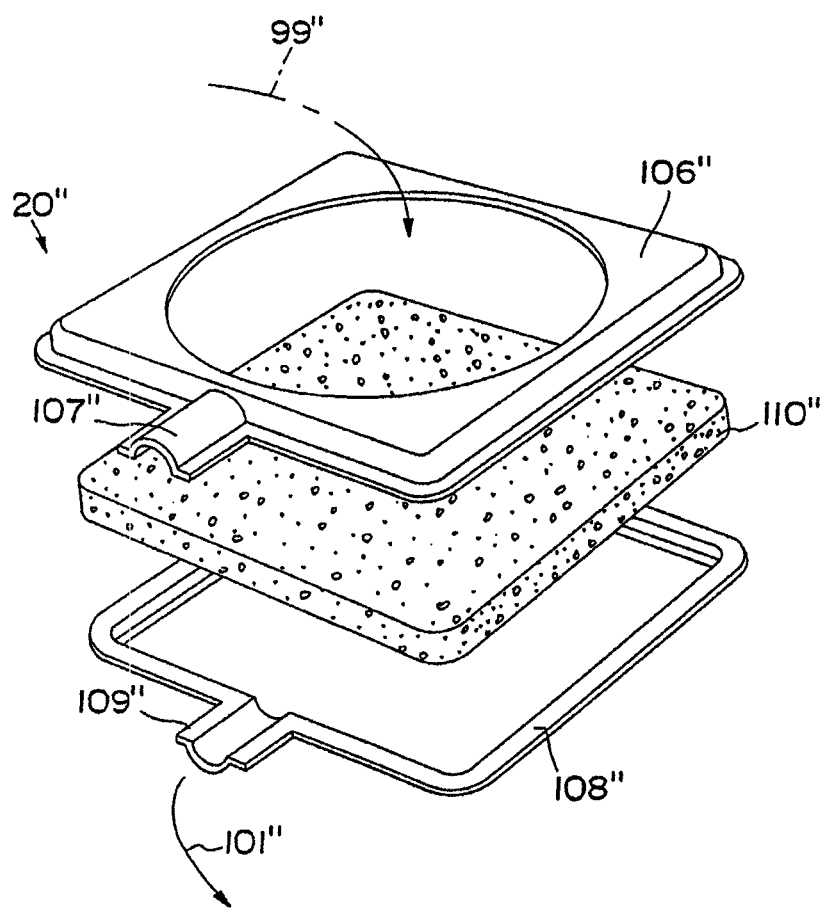
FIG. 14 is an exploded perspective view of an alternative embodiment of a drainage bandage.

Another alternative drainage bandage 20" includes a bottom sheet 106", a top sheet 108", and a pad 110" as shown in FIG. 14. Bottom and top sheets 106", 108" are formed with respective passageway portions 107", 109". Bandage 20" is formed by welding sheets 106", 108" together at their perimeters so that passageway portions 107", 109" form a passageway suitable for coupling to a drainage tube 24. Bandage 20" can be used as discussed above for bandage 20 so that wound effluent from a delivery bandage travels through drainage bandage 20" as shown by arrows 99", 101".

Figure 15:
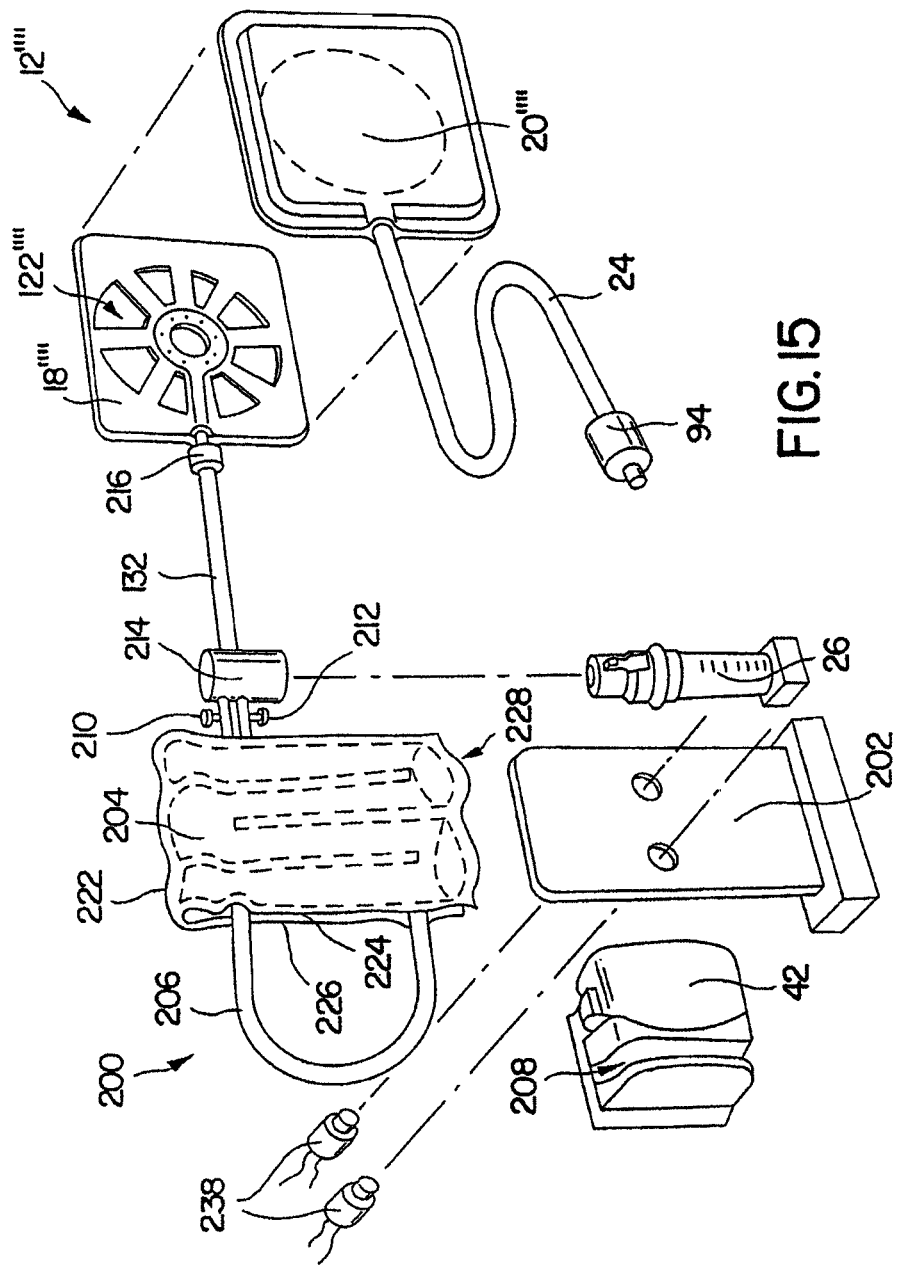
FIG. 15 is a diagrammatic perspective view of an alternative embodiment of a wound treatment apparatus.

As mentioned above, heater 40 can be replaced by other heating systems, such as recirculating fluid heating assembly 200 as shown in FIGS. 15-18. FIG. 15 also shows yet still another alternative embodiment bandage assembly 12"". Bandage assembly 12"" includes a delivery bandage portion 18"" that differs from delivery bandage 18 as shown in FIGS. 4-6 essentially in its outer wound drainage passageways 122"", which are formed as truncated arc segments. Bandage assembly 12"" includes a drainage bandage portion 20"" essentially the same as drainage bandage 20" discussed just above. Bandage assembly 12"" further includes a drainage tube 24 coupled to a wound drainage vapor filter 94.

Heating assembly 200 includes a radiant heating plate 202 configured to be coupled with a recirculating fluid path assembly 204 that transports recirculating fluid in a circuitous path past plate 202. As shown in FIG. 15, fluid path assembly 204 includes a tube section 206 configured to be laced into a channel 208 in a peristaltic pump 42 that pumps the recirculating fluid through assembly 200. Fluid path assembly 204 further includes input and output ports 210, 212 that are coupled to a nebulizer cap 214, which in turn is coupled both to a nebulizer 26 and to a multi-lumen tube 132 leading to bandage assembly 12"". Tube 132 is coupled to bandage assembly 12"" by a connector 216.

Figure 17:
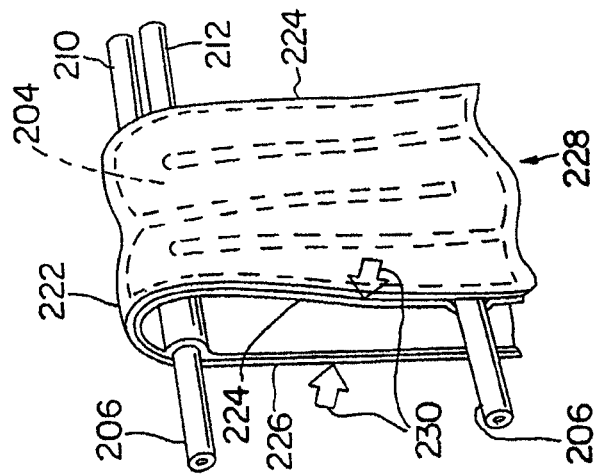
FIG. 17 is a perspective view of the fluid path assembly of FIG. 16.
Figure 16:
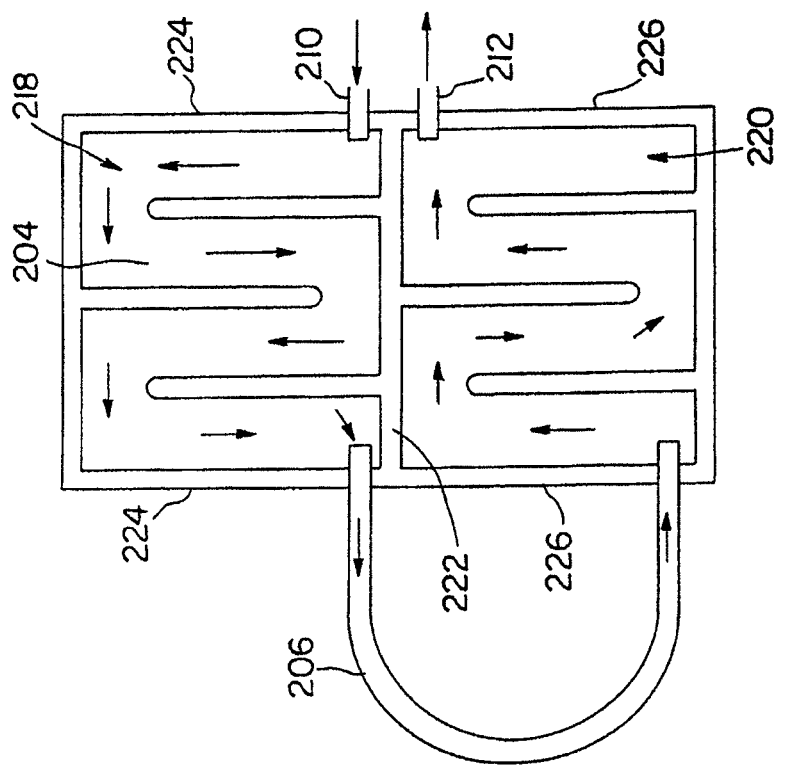
FIG. 16 is a plan view of a recirculating fluid path assembly from the heating assembly of FIG. 15.

Fluid path assembly 204 is illustratively formed by welding two flexible plastic sheets together to form a circuitous fluid input pathway 218 and a circuitous fluid output pathway 220 as shown in FIG. 16. Input pathway 218 is coupled to input port 210 and tube section 206; output pathway 220 is coupled to tube section 206 and output port 212. Fluid path assembly 204 is folded along its centerline 222 as shown in FIG. 17 so that input pathway 218 is opposite output pathway 220. Side edges 224, 226 that extend from centerline 222 are then welded together as shown by arrows 230 to create a pocket 228 configured to receive heating plate 202 so that recirculating fluid travels circuitously through fluid path assembly 204 past heating plate 202.

As fluid flows through fluid path assembly 204 past heating plate 202, fluid temperature is measured, for example, by infrared heat sensors 238. Recirculating fluid temperature is then regulated to a desired value by controlling the heat output of plate 202 selectively based on measured fluid temperature. It is understood that fluid path assembly 204 can be replaced by any suitable mechanism, such as a tube coupled to flexible sheets, or by forming narrow pathways or parallel pathways within flexible sheets, etc. Essentially, the requirement is to provide recirculating fluid pathways capable of receiving heat from plate 202 in order to regulate the temperature of fluid flowing through the pathways.

Figure 18:
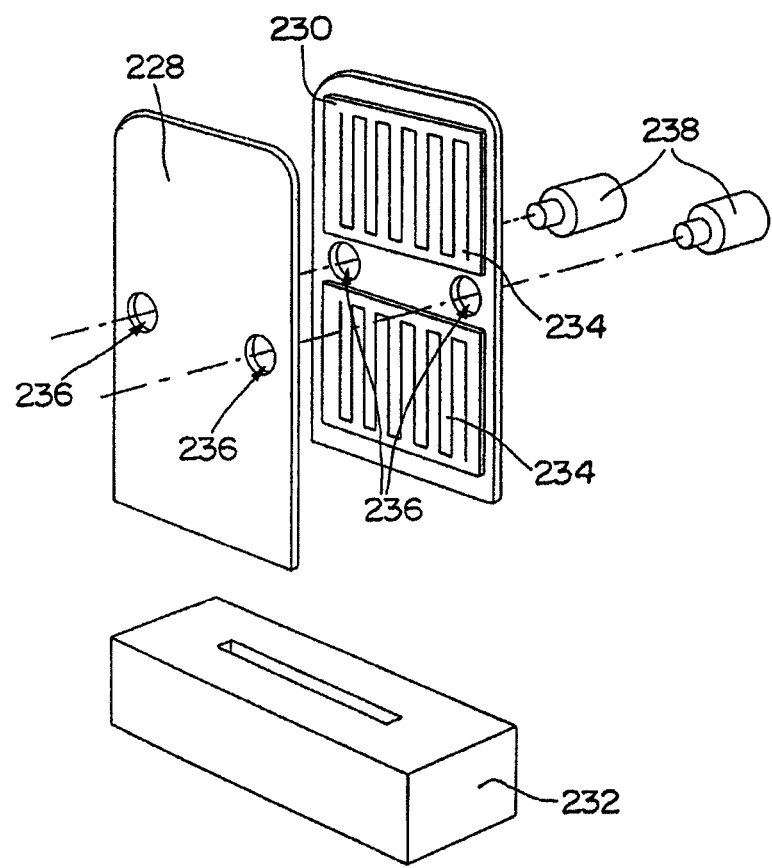
FIG. 18 is an exploded perspective view of the radiant heating plate of the heating assembly of FIG. 15.

Heating plate 202 is illustratively formed from two plate sections 228, 230 that are coupled to a base 232 as shown in FIG. 18. Plate sections 228, 230 include resistive heating elements 234 that are selectively controllable to heat recirculating fluid as it flows in fluid path assembly 204 past plate 202. Plate sections 228, 230 further include holes 236 to facilitate use of infrared temperature sensors for measuring recirculating fluid temperature. Plate 202 and sensors 238 are coupled to control system 44 to provide for automated temperature control of recirculating fluid.

Figure 19:
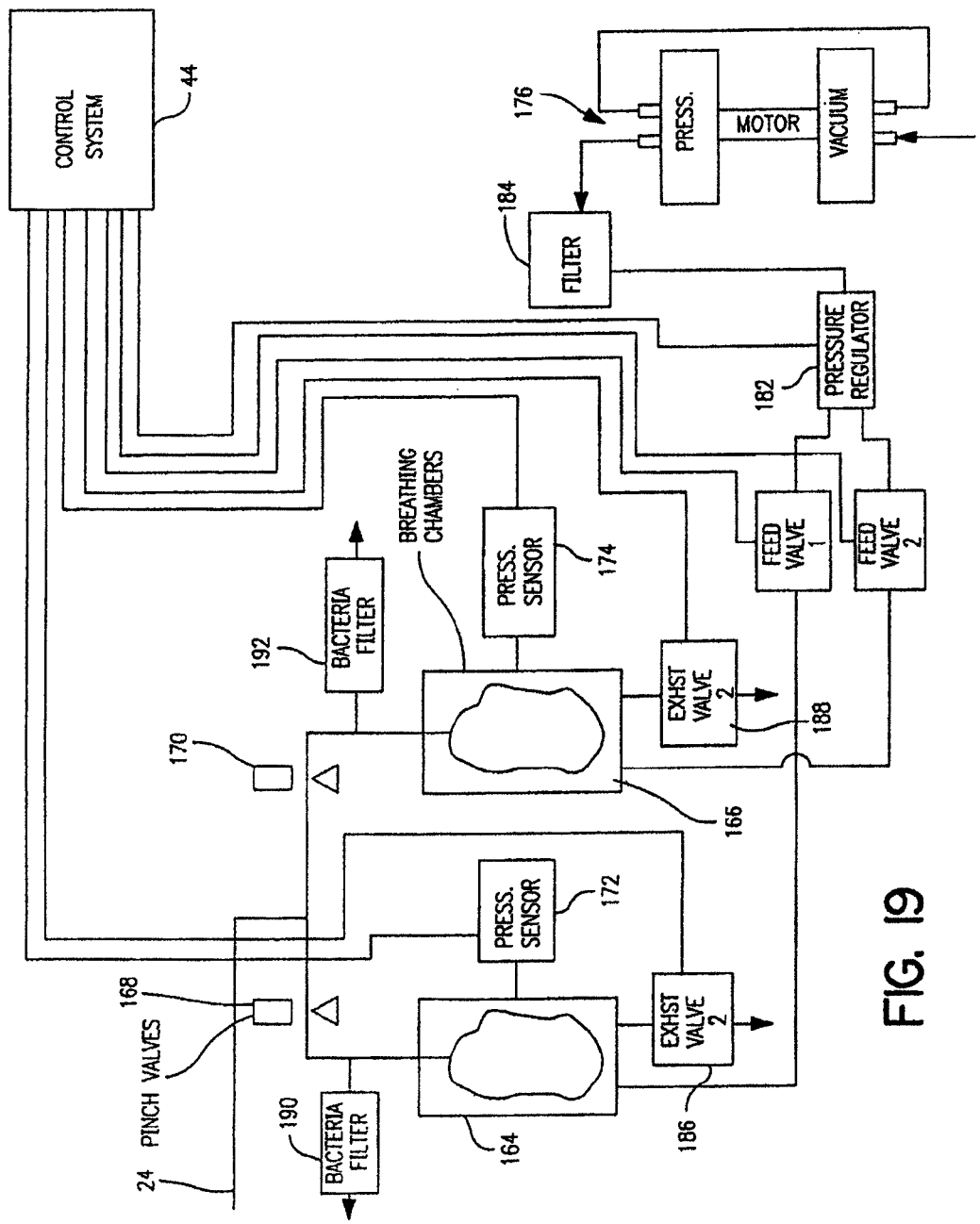
FIG. 19 is a system block diagram of an alternative drainage system embodiment.

An alternative drainage system 162 as shown in FIG. 19 can be used in the wound treatment apparatus 10, 10' of FIGS. 2 and 3 to provide for automated monitoring and switching of drainage bags by control system 44. Drainage system 162 includes first and second drainage bags 164, 166, and valves 168, 170 that are coupled between drainage bags 164, 166 and wound drainage tube 24. Drainage bags 164, 166 include pressure sensors 172, 174 that provide signals to control system 44 indicative of bag pressure, which correlates to whether the bag is full and needs to be changed. Bags 164, 166 further include bacteria filters 190, 192 and exhaust valves 186, 188 that control system 44 can use to vent excess pressure from within bags 164, 166.

Drainage bags 164, 166 are coupled to a pump 176 through valves 178, 180, pressure regulator 182, and filter 184. Valves 168, 170 are coupled to control system 44 to allow for automated selection of which drainage bag will receive effluent from bandage assembly 12, 12'. Drainage system 162 thus allows for automated and continuous operation of wound apparatus 10, 10'. In operation, valve 170 is closed and valve 168 is opened to permit filling of bag 164. When sensor 172 indicates to control system 44 that bag 164 is full, valve 168 is closed and valve 170 is opened to permit filling of bag 166. With valve 168 closed, valve 178 opens to supply pressure to bag 164 to force the contents of bag 164 out through bacteria filter 190. When sensor 174 detects that bag 166 is full, valve 170 is closed and valve 168 is opened to permit filling of bag 164 again. With valve 170 closed, valve 180 opens to supply pressure to bag 166 to force the contents of bag 166 out through bacteria filter 192. This cycle repeats itself so that tube 24 is not exposed to back pressure.

Figures 20, 22:
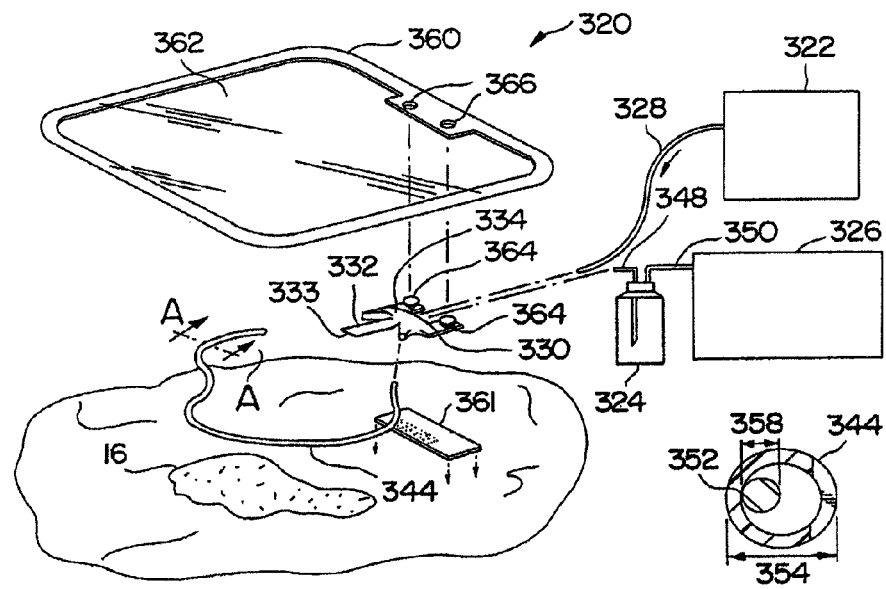
FIG. 20 is an exploded view of a wound treatment assembly and a medicinal fluid supply system including an additional embodiment of the present invention.
FIG. 22 is a sectional view of the circulating fluid tube from the wound treatment assembly of FIG. 20, taken along line A-A.
Figure 21:
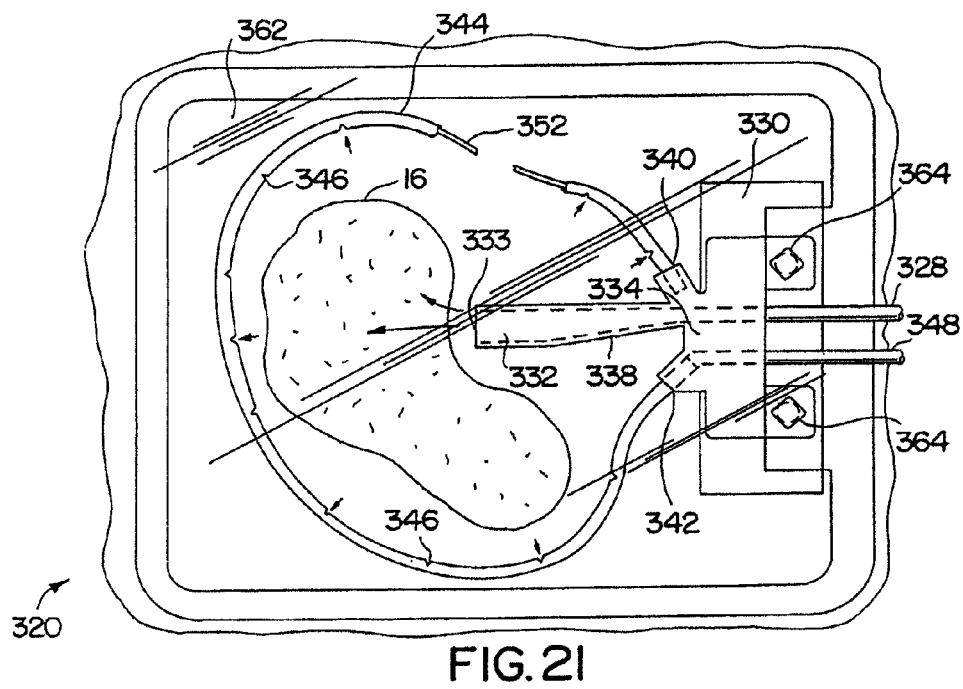
FIG. 21 is a top view of the wound treatment assembly from FIG. 20.

Referring now to FIGS. 20 and 21, an additional embodiment of wound treatment apparatus 320 comprises a medicinal fluid supply 322 to deliver fluid to wound 16, and a vacuum 326 and waste receptacle 324 to draw and store the fluid from wound 16. A supply tube 328 is connected to fluid supply 322 and to a fluid junction array 330. Fluid junction array 330 includes a fluid delivery conduit or deposit membrane 332 having an opening 333, and a circulating tube coupler 334. Opening 333 is positioned near wound 16. Illustratively, deposit membrane 332 can be made from two sheets laterally sealed on each side or it can be made from a simple tube. The material used to make membrane 332 can be rubber, plastic or any other suitable material. In addition, in one illustrative embodiment, membrane 332 has a flare 338 leading to opening 333, as best shown in FIG. 21. Flare 338 allows selective control over the flow rate of the medicinal fluid. The operator may cut membrane 332 thereby reducing its length, and increasing the flow of the medicine. The more flare 338 that is cut off, the faster the flow rate.

Circulating tube coupler 334 illustratively comprises dual ends 340 and 342, respectively. Each end illustratively 340 and 342 extend from opposite sides of membrane 332. (See FIG. 21.) Circulating tube 344 is connected to each end 340 and 342 encircling the periphery of wound 16 on healthy tissue. Fluid collection openings or notches 346 are formed intermittently along the length of tube 344. Illustratively, end 342 is connected to outlet tube 348 whereas end 340 is a terminated end. This forces all of the fluid in tube 344 to travel in one direction toward outlet tube 348. As a result, fluid flows out from membrane 332 passing over wound 16, drawing through notches 346 into tube 344, and exiting through outlet tube 348. Vacuum 326 communicates with outlet tube 348 via vacuum tube 350 and waste receptacle 324 to assist in drawing fluid from wound 16 into waste receptacle 324.

Circulating tube 344 may include a bendable wire 352 extending therethrough. Bendable wire 352 provides a semi-ridged form for tube 344 so that it may be selectively positioned about the periphery of wound 16 and hold its shape. As shown in FIG. 22, diameter 358 of bendable wire 352 is less than inner diameter 354 of circulating tube 344, thereby not inhibiting the flow of fluid.

Fluid junction array 330 attaches to adhesive 361 which adheres to a portion of healthy tissue surrounding wound 16. It is appreciated, however, that array 330 may be attached to the skin by any variety of suitable means. Top sheet 362 is sized to cover apparatus 320 and may be removably attached directly to healthy skin (not shown). Top sheet 362 is illustratively formed from a clear, flexible polyurethane or vinyl that meets USP Class VI requirements for medical applications. Gasket or border 360 is illustratively formed with a generally square perimeter having rounded corners attaching to the skin about the periphery of tube 344 and serves as a seal. In one embodiment, border 360 is positioned underneath top sheet 362, as shown in FIG. 21. In addition, border 360 attaches to array 330 by a pair of fasteners 364 that extend through apertures 366.

Another embodiment of the wound treatment apparatus is indicated by reference number 368 and is shown in FIGS. 23 and 24. A fluid supply tube 382 leads illustratively into outer chamber 378. Outer chamber 378 is formed about the periphery of inner chamber 374. Chambers 374 and 378 are formed by a top sheet and a bottom sheet 372 and 373, respectively. (See FIG. 24.) Illustratively, RF welds about the periphery of inner chamber 374 and about the periphery of outer chamber 378 further defines the chambers within sheets 372 and 373. The welds form an inner border and an outer border 375 and 380, respectively. It is understood that any suitable means can be used to form borders 375 and 380, in place of ultra-sonic welds. For example, borders 375 and 380 can be made from adhesive or from heat selectively applied to sheets 372 and 373.

A gasket 383 is attached about outer border 380 of the bandage. Gasket 383 suspends sheets 372 and 373 forming a wound cavity 379 as shown in FIG. 24. An adhesive 384 is attached to the underside of gasket 383 to adhere to healthy skin tissue surrounding the wound (not shown) thereby holding apparatus 368 in place and containing the medicinal fluid in wound cavity 379.

Illustratively, medicinal fluid is deposited through tube 382 into outer chamber 378. Several passageways 377 are disposed, in spaced relation to each other, through lower sheet 373 into wound cavity 379. Medicinal fluid can then flow through passageways 377 into wound cavity 379 and onto the wound. The fluid is then drawn from the surface of the wound up through outlet aperture 376. Outlet aperture 376 is disposed through lower sheet 373 into inner chamber 374. With the assistance of a vacuum connected to outlet tube 370, the medicinal fluid is drawn from inner chamber 374 into tube 370 and ultimately into a waste receptacle. Fluid collection openings or notches 346 are formed intermittently along the length of tube 370 within inner chamber 374 to further assist in collecting fluid.

It is appreciated that the flow direction of the medicinal fluid may be reversed from that previously described. Illustratively, medicinal fluid can enter apparatus 368 through outlet tube 370, and dispense through aperture 376 into wound cavity 379. Fluid can then be drawn through apertures 377 into outer chamber 378 and out through tube 382. Apertures 377 may be of any size suitable to draw the fluid from wound cavity 379 into chamber 378.

A still further embodiment of the wound treatment apparatus is indicated by reference number 386 and is shown in FIGS. 25 and 26. In contrast to the previous embodiment, fluid supply tube 382 leads illustratively into inner chamber 374. Like the previous embodiment, outer chamber 378 is formed about the periphery of inner chamber 374. In addition, chambers 374 and 378 are formed by a top sheet and a bottom sheet 372 and 373, respectively. (See FIG. 26.) Again, illustratively, an RF weld about the periphery of inner chamber 374 and at the periphery outer chamber 378 further defines the chambers within sheets 372 and 373. The welds form an inner border and an outer border 375 and 380, respectively. It is understood that any suitable means can be used to form borders 375 and 380, in place of RF welds.

Illustratively, medicinal fluid is deposited through tube 382 into inner chamber 374. This is in contrast to the previous embodiment where tube 382 deposited fluid into outer chamber 378. Medicinal fluid can then flow through inlet aperture 385 that is disposed through bottom sheet 373 into wound cavity 379 and onto the wound. Several passageways 381 are disposed, in spaced relation to each other, through lower sheet 373 into wound cavity 379. In one illustrative embodiment, passageways 381 are larger in size than passageways 377 in the previous embodiment. The fluid is drawn from the surface of the wound up through passageways 381. In one embodiment, openings or notches 346 are formed intermittently along the portion of tube 391 extended within outer chamber 378. Tube 391 illustratively extends through outer chamber 380. With the assistance of a vacuum connected to outlet tube 391, the medicinal fluid is drawn up from outer chamber 378 into tube 391 and ultimately into a waste receptacle. Other features like gasket 383 and adhesive 384 are configured similar to that of the previous embodiment.

It is appreciated that the flow direction of the medicinal fluid may be reversed from that previously described. Illustratively, medicinal fluid can enter apparatus 386 through tube 391, flow out notches 388 and dispense through apertures 381 into wound cavity 379. Fluid can then be drawn through aperture 385 into inner chamber 374 and out through tube 382. Apertures 381 may be of any size suitable to dispense the fluid from outer chamber 378 into wound cavity 379.

An additional embodiment of a wound treatment apparatus is indicated by reference number 392 and is shown in FIGS. 27-29. Wound apparatus 392 comprises a fluid supply tube 396 extending illustratively near the center of apparatus 392 into a dispensing aperture 398. Aperture 398 opens to a wound cavity 400 formed on the underside of apparatus 392. (See FIGS. 28 and 29.) Above wound cavity 400 and formed about dispensing aperture 398 is basin 402. Basin 402 is defined by inner and outer walls 410 and 412, respectively. Inner wall 410 separates the basin 402 from dispensing aperture 398. Outer wall 412 illustratively defines the periphery of basin 402. Columns 404 extend from basin 402, illustratively in a circular formation about inner wall 410, as shown in FIG. 27. A top sheet 405 is formed over basin 402, attaching illustratively to the top of outer wall 412. Columns 404 support top sheet 405 over basin 402. Top sheet 405 is thereby prevented from collapsing in on basin 402 and covering passageways 406 as a negative pressure is applied to bandage 392.

An adhesive 394 is attached to apparatus 392 illustratively about the periphery of cavity 400. As with previous embodiments, adhesive 394 adheres to healthy skin tissue surrounding the wound. It is appreciated that adhesive 394 may be replaced with any variety of means to secure wound apparatus 392 over the wound.

Illustratively, medicinal fluid flows from tube 396 through aperture 398 into wound cavity 400 and onto the wound. The fluid then draws up through passageways 406 collecting in basin 402. The collected fluid is then drawn from basin 402 into outlet tube 414 and ultimately into a waste receptacle (not shown). As with other embodiments previously discussed, a vacuum may illustratively be attached to outlet tube 414 in the manner previously described.

It is appreciated, however, that the flow direction of the medicinal fluid in apparatus 392 may be reversed from that previously described. Illustratively, medicinal fluid can enter through tube 414, flow into wound cavity 400 through passageways 406. The fluid can then be drawn through aperture 398 into tube 396. Apertures 406 may be of any size suitable to dispense or draw the fluid to or from wound cavity 400.

Figure 30:
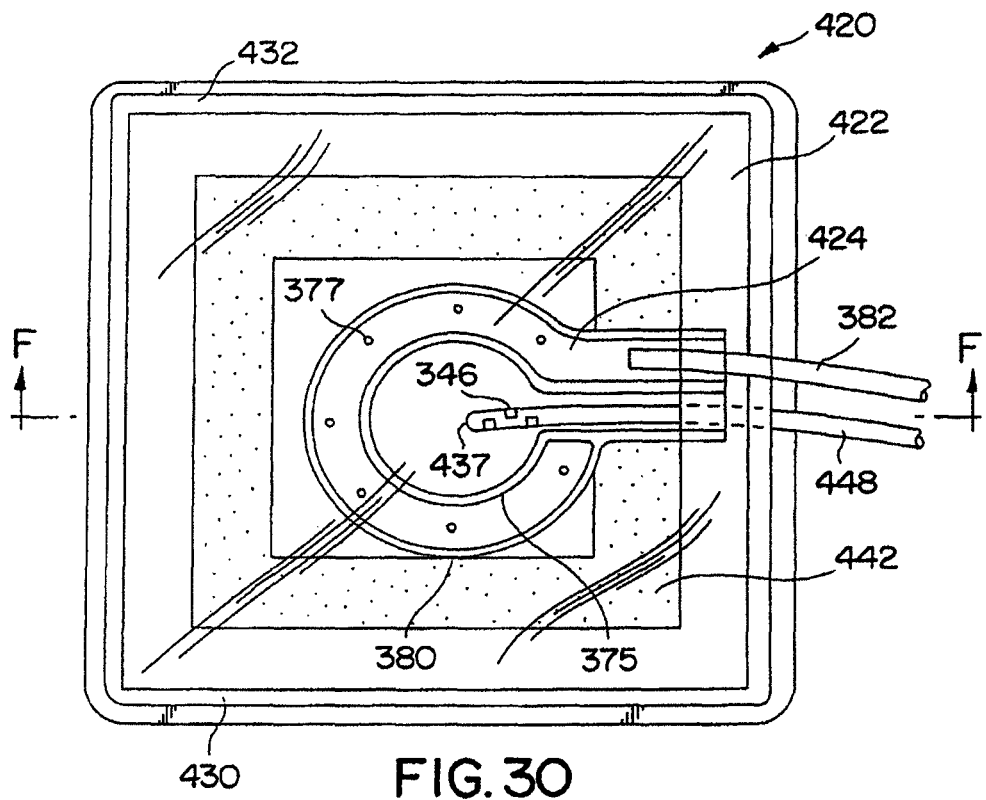
FIG. 30 is a top view of a flexible wound treatment assembly in accordance with the present invention.
Figure 31:
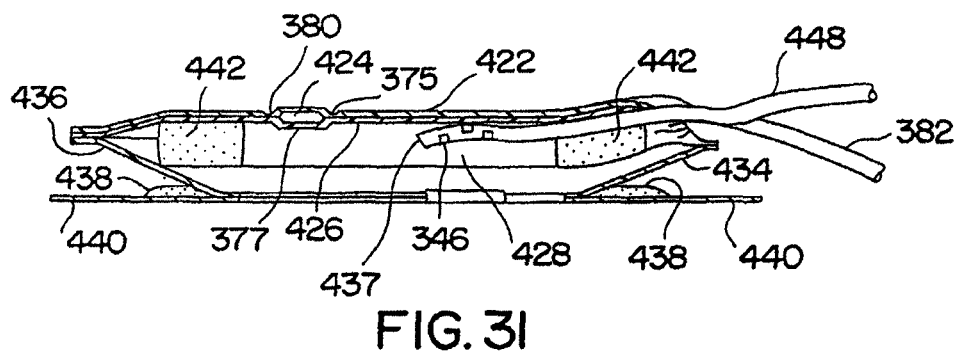
FIG. 31 is a sectional view of the flexible wound treatment assembly from FIG. 30, taken along line F-F.
Figure 32:
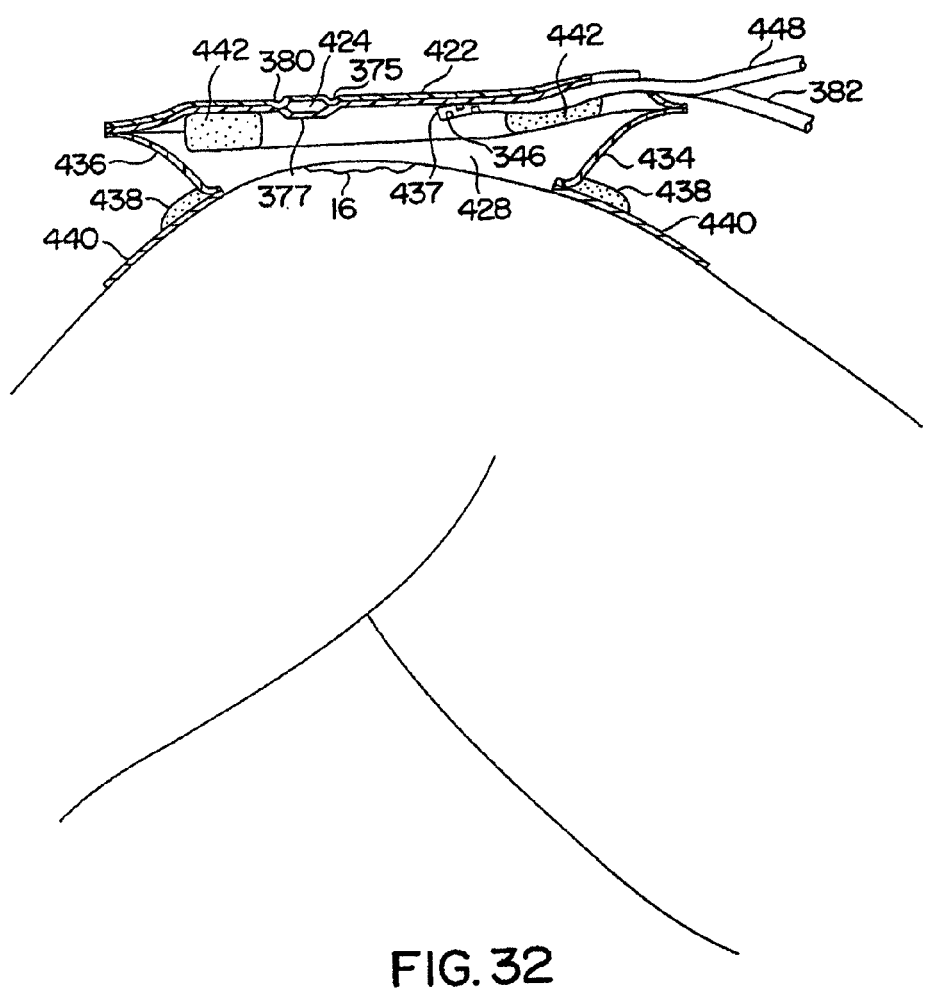
FIG. 32 is a sectional view of the flexible wound treatment assembly from FIG. 31, applied over a wound on a bendable joint.

Another embodiment of the present invention includes a flexible wound treatment apparatus 420 shown in FIGS. 30-32. An inlet tube 382 is extended through top panel 422 into chamber 424. Chamber 424 is formed between top panel 422, mid-panel 426, and is defined by inner and outer borders 375 and 380, respectively. (See FIGS. 30 and 31.) Illustratively, an RF weld about the peripheries of chamber 424 forms borders 375 and 380 as previously discussed. Several apertures 377 are disposed through mid-panel 426 into an expanded wound cavity 428. Wound cavity 428 is defined by two laterally spaced side walls 430 and 432 and two end walls 434 and 436 extending between said side walls 430 and 432. Mid-panel 426 interconnects to the coplanar edges of walls 430, 432, 434, and 436. The resultant form is a flexible bellow or flexible body. A spacer 442 is fitted within the periphery of wound cavity 440. Spacer 442 is illustratively made from a foam material but it is understood that it can be made from any suitable material that will assist in maintaining the form of the expanded wound cavity 428 as shown in FIGS. 31 and 32.

Formed about the periphery of wound cavity 428 and attached to coplanar edges of said walls 430, 432, 434, and 436 opposite mid panel 426, is a pad 438. Pad 438 is illustratively made from a thin flexible foam material and often with a plastic-like top coating. Pad 438 provides a cushioning intermediary between the walls 430, 432, 434, and 436, and an adhesive 440. Adhesive 440, is a similar panel to those adhesives described in the previous embodiments.

Flexible wound treatment apparatus 420 is optimum for use on flexible joints like knees and elbows. This is because spacer 442 keeps mid-panel 426 raised enough so that as wound 16 is raised as the joint bends, wound 16 will not be interfered with by mid-panel 426. (See FIG. 32.)

Illustratively, and in similar fashion to previous embodiments, tube 382 deposits medicinal fluid into chamber 424 where it flows through passageways 377 into cavity 428. An outlet tube 448 is extended illustratively through top panel 422, over spacer 442, and into wound cavity 428. Notches 346 can be formed in the length of tube 448 positioned within cavity 428 so that after the fluid has deposited onto wound 16 it is drawn up through opening 437 and/or notch 346 into outlet tube 448. Like previous embodiments, it is understood that the flow of the medicinal fluid can be reversed. The fluid can be deposited onto wound 16 by tube 448 and drawn up through passageways 377 into chamber 424 and out tube 382.

Figure 33:
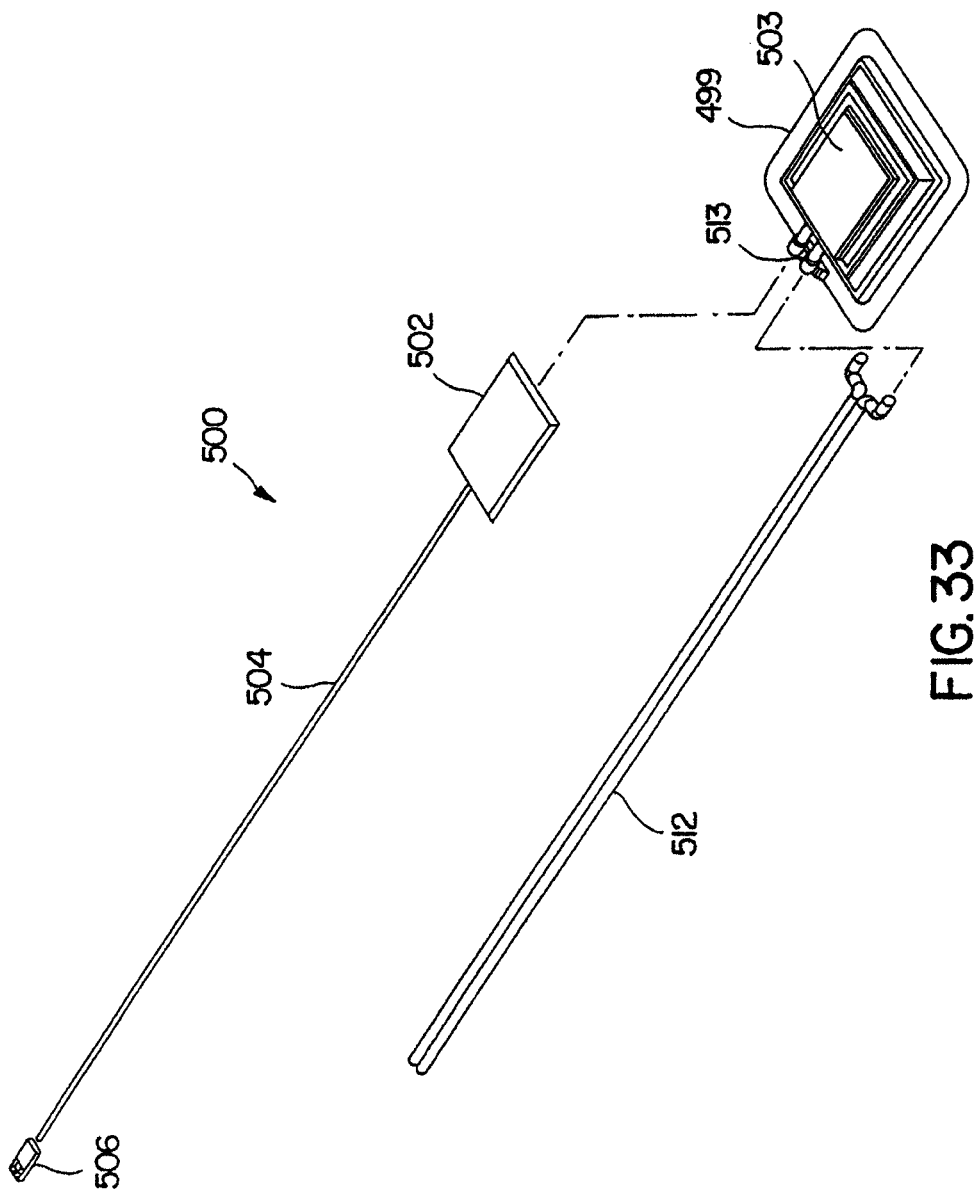
FIG. 33 is a perspective view of a wound treatment apparatus including a heating system.
Figure 34:
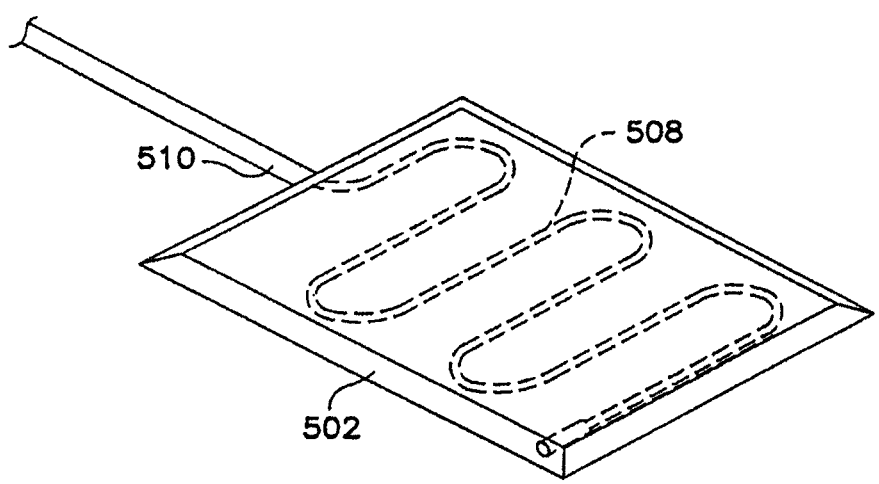
FIG. 34 is a perspective clear view of a portion of the wound treatment apparatus from FIG. 33.

A further embodiment of the present invention comprises a heat and heat sensing system 500 (collectively, heat system 500) coupled, illustratively, with bandage 499 as shown in FIG. 33. It is appreciated that heat system 500 can be coupled with any bandage described herein. Heat system 500 includes a heating and sensing pad 502, thermocouples 508 and 510, a tube assembly 504, and a patch unit connector 506. Pad 502 is the portion of system 500 that transfers heat to bandage 499 as well as senses the amount of heat that was transferred. Illustratively, pad 502 includes a thermocouple 508 that supplies heat to pad 502, See FIG. 34. A second thermocouple 510 senses the heat that is being supplied by thermocouple 508. Pad 502 can be made, illustratively from silicone, but it is appreciated that pad 502 can be made from any suitable material serving the same function as silicone. Pad 502 can be either inserted into a pocket 503 within the bandage or coupled to the bandage by any suitable means. In addition, alternatives to pad 502 can be used to transfer heat from thermocouple 508 to bandage 499. Both thermocouples 508 and 510 extend from pad 502 to patch unit connector 506. Illustratively, the thermocouples can be contained in tube 504 protecting same. Tube 504 can be flexible and made from any suitable material, and be of any suitable length.

Patch connector 506 connects to a nebulizer cartridge (not shown) and can be removed for continual use on additional bandages. A double lumen tube 512 can connect to tube connector 513 to supply medicinal fluid to bandage 499 and draw fluid away from same, as hereinbefore described.

Although the invention has been described in detail with reference to certain preferred embodiments, variations and modifications exist within the scope and spirit of the present invention as described and defined in the following claims.

We claim:

1. A wound treatment apparatus for use with a vacuum source for providing negative pressure, comprising:
a bandage including a first sheet configured to overlie a wound and having a plurality of discrete passageways configured to communicate negative pressure to the wound, a top sheet overlying the first sheet, a foam pad positioned between the first sheet and the top sheet, and a fluid drainage tube in fluid communication with the plurality of discrete passageways;
first and second fluid drainage receptacles fluidly coupled to the fluid drainage tube and configured to be coupled to a vacuum source for providing negative pressure to the wound; and
first and second inlet valves actionable to be closed or opened between the fluid drainage tube and the first and second fluid drainage receptacles, respectively, and operable when the vacuum source is coupled to the first and second fluid drainage receptacles such that negative pressure is delivered from the vacuum source to the first drainage receptacle and the fluid drainage tube when the first inlet valve is open and the second inlet valve is closed, and to the second drainage receptacle and the fluid drainage tube when the second inlet valve is open.

2. The apparatus of claim 1, wherein the inlet valves are pinch valves.

3. The apparatus of claim 1, further comprising a controller electrically coupled to the first and second inlet valves, the controller configured to select which of the first and second fluid drainage receptacles receives fluid from the fluid drainage tube.

4. The apparatus of claim 3, further comprising a first sensor coupled to the first fluid drainage receptacle to provide a signal to the controller indicative of an amount of fluid in the first fluid drainage receptacle.

5. The apparatus of claim 4, further comprising a second sensor coupled to the second drainage receptacle to provide a signal to the controller indicative, of an amount of fluid in the second fluid drainage receptacle.

6. The apparatus of claim 5, where the first and second sensors are pressure sensors.

7. The apparatus of claim 1, further comprising a first exhaust valve coupled to the first fluid drainage receptacle such that the first exhaust valve can be opened to vent excess pressure from the first fluid drainage receptacle.

8. The apparatus of claim 7, further comprising a second exhaust valve coupled to the second fluid drainage receptacle such that the second exhaust valve can be opened to vent excess pressure from the second fluid drainage receptacle.

9. The apparatus of claim 8, further comprising a controller electrically coupled to the first and second exhaust valves and configured to selectively open and close the first and second exhaust valves.

10. The apparatus of claim 1, further comprising a first outlet valve coupled between the first fluid drainage receptacle and the vacuum source for providing a negative pressure to drain the first fluid drainage receptacle when the first inlet valve is closed.

11. The apparatus of claim 10, further comprising a second outlet valve coupled between the second fluid drainage receptacle and the vacuum source for providing a negative pressure to drain the second fluid drainage receptacle when the second inlet valve is closed.

12. The apparatus of claim 11, further comprising a controller electrically coupled to the first and second inlet valves and outlet valves and configured to selectively open and close the first and second inlet valves and outlet valves.

13. The apparatus of claim 12, wherein the controller is configured to open the first inlet valve and close the first outlet valve to fill the first fluid drainage receptacle.

14. The apparatus of claim 13, wherein the controller is configured to close the second inlet valve to prevent the second fluid drainage receptacle from filling.

15. The apparatus of claim 14, wherein the controller is configured to provide an indication when the first fluid drainage receptacle is filled.

16. The apparatus of claim 12, wherein the controller is configured to close the first inlet valve and open the first outlet valve to drain the first fluid drainage receptacle.

17. The apparatus of claim 16, wherein the controller is configured to open the second inlet valve and close the second outlet valve to fill the second fluid drainage receptacle.

18. The apparatus of claim 17, wherein the controller is configured to close the second inlet valve and open the second outlet valve to drain the second fluid drainage receptacle.

19. The apparatus of claim 1, wherein the negative pressure is delivered from the vacuum source alternately to the first drainage receptacle and the second drainage receptacle when the second inlet valve is opened and the first inlet valve is closed.

20. The apparatus of claim 19, further comprising a first outlet valve coupled between the first fluid drainage receptacle and the vacuum source for providing a negative pressure to drain the first fluid drainage receptacle when the first inlet valve is closed.

21. The apparatus of claim 20, further comprising a second outlet valve coupled between the second fluid drainage receptacle and the vacuum source for providing a negative pressure to drain the second fluid drainage receptacle when the second inlet valve is closed.

22. The apparatus of claim 21, further comprising a controller electrically coupled to the first and second inlet valves and outlet valves and configured to selectively open and close the first and second inlet valves and outlet valves.

23. The apparatus of claim 22, wherein the controller is configured to open the first inlet valve and close the first outlet valve to fill the first fluid drainage receptacle.

24. The apparatus of claim 23, wherein the controller is configured to close the second inlet valve to prevent the second fluid drainage receptacle from filling.

25. The apparatus of claim 24, wherein the controller is configured to provide an indication when the first fluid drainage receptacle is filled.

26. The apparatus of claim 22, wherein the controller is configured to close the first inlet valve and open the first outlet valve to drain the first fluid drainage receptacle.

27. The apparatus of claim 26, wherein the controller is configured to open the second inlet valve and close the second outlet valve to fill the second fluid drainage receptacle.

28. The apparatus of claim 27, wherein the controller is configured to close the second inlet valve and opened the second outlet valve to drain the second fluid drainage receptacle.

29. A wound treatment apparatus for use with a vacuum source for providing negative pressure, comprising:
a bandage including a first sheet configured to overlie a wound and having a plurality of discrete passageways configured to communicate negative pressure to the wound, a top sheet overlying the first sheet, a foam pad positioned between the first sheet and the top sheet, and a fluid drainage tube in fluid communication with the plurality of discrete passageways;

first and second fluid drainage receptacles fluidly coupled to the fluid drainage tube and configured to be coupled to a vacuum source for providing negative pressure to the wound; and first and second inlet valves actionable to be closed or opened between the fluid drainage tube and the first and second fluid drainage receptacles, respectively, and operable when the vacuum source is coupled to the first and second fluid drainage receptacles such that negative pressure is delivered from the vacuum source to the first drainage receptacle and the fluid drainage tube when the first inlet valve is open and the second inlet valve is closed, and to the second drainage receptacle and the fluid drainage tube when the second inlet valve is open and the first inlet valve is closed.

30. A wound treatment apparatus comprising:

a bandage including a first sheet configured to overlie a wound and having a plurality of discrete passageways configured to communicate negative pressure to the wound, a top sheet overlying the first sheet, a foam pad positioned between the first sheet and the top sheet, and a fluid drainage tube in fluid communication with the plurality of discrete passageways;

first and second fluid drainage receptacles fluidly coupled to the fluid drainage tube and adapted to be fluidly coupled to a vacuum source to communicate negative pressure to the first and second fluid drainage receptacles;

first and second inlet valves actionable to be closed or opened between the fluid drainage tube and the first and second fluid drainage receptacles, respectively, and operable when the vacuum source is coupled to the first and second fluid drainage receptacles such that negative pressure is delivered from the vacuum source to the first drainage receptacle and the fluid drainage tube when the first inlet valve is open and the second inlet valve is closed, and to the second drainage receptacle and the fluid drainage tube when the second inlet valve is open and the first inlet valve is closed; and an outlet valve coupled between either one of the first and second fluid drainage receptacles and a vacuum source for providing a negative pressure to drain either one of the first and second fluid drainage receptacles when the corresponding one of the first and second inlet valves is closed.

* * * * *